(12) United States Patent
Chandrasekaran et al.

(10) Patent No.: US 10,988,434 B2
(45) Date of Patent: Apr. 27, 2021

(54) FRAGRANCE MIXTURE

(71) Applicant: SYMRISE AG, Holzminden (DE)

(72) Inventors: Vijayanand Chandrasekaran, Holzminden (DE); Johannes Panten, Höxter (DE); Oskar Koch, Göttingen (DE); Edison Diaz Gomez, Goslar (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/471,422

(22) PCT Filed: Sep. 27, 2017

(86) PCT No.: PCT/EP2017/074461
§ 371 (c)(1),
(2) Date: Sep. 19, 2019

(87) PCT Pub. No.: WO2018/114073
PCT Pub. Date: Jun. 28, 2018

(65) Prior Publication Data
US 2020/0010402 A1 Jan. 9, 2020

(30) Foreign Application Priority Data
Dec. 21, 2016 (EP) ..................... 16205788

(51) Int. Cl.
| | | |
|---|---|---|
| *A61K 8/18* | (2006.01) | |
| *A61Q 13/00* | (2006.01) | |
| *A61K 8/00* | (2006.01) | |
| *C07C 69/593* | (2006.01) | |
| *C07C 51/56* | (2006.01) | |
| *C07C 67/12* | (2006.01) | |
| *C07C 67/333* | (2006.01) | |
| *C07D 307/36* | (2006.01) | |

(52) U.S. Cl.
CPC ............ *C07C 69/593* (2013.01); *C07C 51/56* (2013.01); *C07C 67/12* (2013.01); *C07C 67/333* (2013.01); *C07D 307/36* (2013.01); *A61Q 13/00* (2013.01)

(58) Field of Classification Search
CPC ..... C07C 69/593; C07C 67/333; C07C 67/12; C07C 51/56; C07C 57/13; C11D 3/50; C11D 7/266; A61K 8/37; A23L 27/2028; C11B 9/0019; A61Q 13/00; A61Q 17/04; A61Q 15/00; A61Q 5/12; A61Q 5/02; A61Q 5/10; A61Q 19/00
USPC .................................. 512/26, 25, 1
See application file for complete search history.

(56) References Cited

U.S. PATENT DOCUMENTS 3,488,419 A 1/1970 McCune et al.
3,976,801 A 8/1976 Hall et al.

FOREIGN PATENT DOCUMENTS

| CN | 102628837 | * | 6/2011 |
|---|---|---|---|
| DE | 2224430 A1 | | 12/1973 |
| DE | 2343196 A1 | | 4/1975 |
| EP | 1188433 A2 | | 3/2002 |
| EP | 1332772 A2 | | 8/2003 |
| EP | 1332772 A3 | | 11/2004 |
| JP | 02157209 | * | 6/1990 |
| JP | H02157209 A | | 6/1990 |
| JP | H11009675 A | | 1/1999 |
| WO | WO-2003/043431 A1 | | 5/2003 |
| WO | WO-2004/084853 A2 | | 10/2004 |
| WO | WO-2015/091924 A1 | | 6/2015 |

OTHER PUBLICATIONS

Wei et al, CN 102628837 Machine Translation, Jun. 23, 2011 (Year: 2011).*
Amaya et al, JP 02157209 Machine Translation, Jun. 18, 1990 (Year: 1990).*
Balasubramaniyan et al., "Facile esterification of carboxylic acids with organophosphorus reagents: Novel application of alkylphosphoric esters (ape)," Tetrahedron 39(9):1475-1485 (1983).
Brenna et al., "Steric Effects on the Stereochemistry of Old Yellow Enzyme-Mediated Reductions of Unsaturated Diesters: Flipping of the Substrate within the Enzyme Active Site Induced by Structural Modifications," Adv. Synth. Catal. 354:2859-2864 (2012).
Cooke, Jr., "New Ylide Anions. A Vinyl Anion Equivalent for Substituted Fumarate Esters," Tetrahedron Letters 22:381-384 (1981).
Harris et al., "Acylphosphonates as Substrates for Wittig and Horner-Wittig Reactions. Unusual Stereoselectivity in the Synthesis of β-Phosphinoylacrylates," Aust. J. Chem. 37:417-24 (1984).
Jennings, "New fruit esters and the flavor of Bartless pears," Ber. Int. Fruchtsafe-Union, Wiss. Tech. Komm. 6:277-87, Abstract(1965).
Liu et al., "Ligand-Controlled Palladium-Catalyzed Alkoxycarbonylation of Allenes: Regioselective Synthesis of α,β- and β,γ-Unsaturated Esters," J. Am. Chem. Soc. 137:8556-8563 (2015).
Maury et al., "Unprecedented Noncatalyzed anti-Carbozincation of Diethyl Acetylenedicarboxylate through Alkylzinc Group Radical Transfer," Organic Letters 13(7):1884-1887 (2011).
Petri, "Contribution to the knowledge of itaconic acid, measoconic acid and citraconic acid," Chemical Institute of the University of Bonn. (1881).
Saisaha et al., "Manganese catalyzed cis-dihydroxylation of electron deficient alkenes with $H_2O_2$," Org. Biomol. Chem. 8:4444-4450 (2010).

(Continued)

*Primary Examiner* — Jessica Whiteley
(74) *Attorney, Agent, or Firm* — Marshall, Gerstein & Borun LLP

(57) ABSTRACT

A fragrance mixture and its applications, in particular perfume oils, cosmetic agents, application agents or washing and cleaning agents, containing a sensory effective amount of (i) (E)-2-methyl-but-2-endicarboxylic acid diethyl ester, (ii) (Z)-2-methyl-but-2-endicarboxylic acid diethyl ester or (iii) 2-methylenebutanedicarboxylic acid diethyl ester and mixtures thereof and analogous esters derived from these compounds and mixtures.

14 Claims, No Drawings

(56) References Cited

OTHER PUBLICATIONS

Sharma et al., "Exploration of the Molecular Origin of the Azinomycin Epoxide: Timing of the Biosynthesis Revealed," Organic Letters 10(21):4815-4818 (2008).
Tripp et al., "Stereochemistry of Hexenyl Radical Cyclizations with tert-Butyl and Related Large Groups: Substituent and Temperature Effects," J. Am. Chem. Soc. 127:5518-5527 (2005).
Tsai, "Synthesis of Phenyl Substituted Fluoro-Olefins," Tetrahedron Letters 37(5):629-632 (1996).
Weis et al., "Rhodium-katalysierte Isomerisierungen von 2-Methylidenglutar-säureestern zu Methylglutaconsäureestern," Helvetica Chimica Acta 57(3):856-863 (1974).
Wenkert et al., "7-Dimethylvinylidene-1-methoxybicyclo[4.1.0]heptane and Ethyl 1-Ethoxy-2-methylcyclopropane-3-carboxylate," Synthetic Communications 7(6):375-382 (1977).

\* cited by examiner

FRAGRANCE MIXTURE

The invention is in the field of fragrances and concerns fragrance mixtures with a fruity, pear-like note, preparations containing special fragrances or fragrance mixtures, processes for producing special fragrances with a pear-like note, a perfuming process and the use of special fragrances to produce a pear-like scent note.

Despite a large number of existing fragrances, the perfume industry still has a general need for new fragrances. In particular, there is a need for fragrances which are not only characterized by new and original scent notes, but also have additional positive secondary properties in addition to their olfactory properties, such as greater stability and extensiveness under certain conditions of use, better adhesion, greater radiance, a lower threshold value or better dermatological and toxicological results, such as good biodegradability.

In particular, there is a need for fragrances which, at a lower dosage, contribute the same or a higher scent contribution than comparable substances and thus lead to a lower input into the environment (low volume-high impact). Or which can be made available at a much lower price with the same scent contribution. There is a special need here for fragrances with complex olfactory properties, such as fruity pear-like. However, acetic acid amyl ester, which is otherwise known for its pear-like aroma, does not fulfill these conditions.

The task of the present study was therefore to provide fragrances and perfume compositions with pear-like aroma on the basis of renewable raw materials, preferably waste products, which overcome the aforementioned disadvantages of the state of the art, i.e. in particular already in low dosages, provide a high scent contribution, can be easily and stably incorporated into various perfume and end product formulations and can be produced with little technical effort and at low cost.

GENERAL DESCRIPTION OF THE INVENTION

A first object of the invention concerns a fragrance mixture containing a sensory effective amount of one, two or all three compounds from the group formed by: formula (i), formula (ii), and formula (iii):

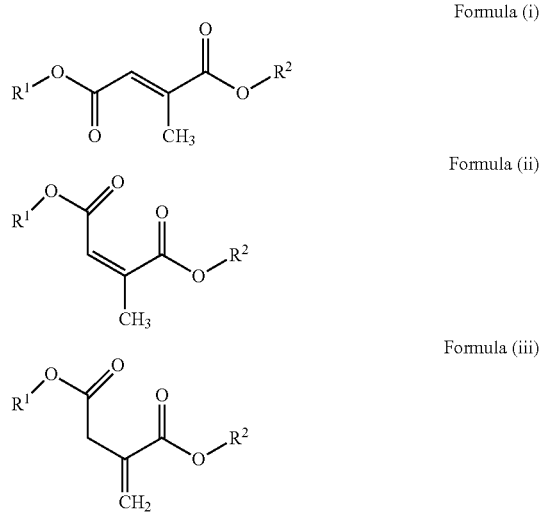

Formula (i)

Formula (ii)

Formula (iii)

wherein R1 each represents a linear, branched or cyclic alkyl group having 1 to 10 carbon atoms, preferably a methyl or ethyl group, an araliphatic or aromatic group, and R2 each represents a linear, branched or cyclic alkyl group having 1 to 10 carbon atoms, preferably a methyl or ethyl group, an araliphatic or aromatic group.

Surprisingly, it was found that in particular the compounds of formula (i) are suitable as pear-like fragrances and fully meet the complex requirement profile described above. The substances of formula (ii) and formula (iii) are present during manufacture and also have an attenuated pear-like aroma. It is particularly noteworthy that these substances are obtained from renewable raw materials, especially from waste from the sugar industry. It was also surprising that these substances can be incorporated into a large number of different formulations in a permanently stable manner and in particular exceed the standard of ethyl decadienoates.

Preferably R1 and R2 are each an identical or different linear, branched or cyclic alkyl radical having 1 to 8 or 1 to 6 carbon atoms, preferably a methyl or ethyl radical. The linear radicals are particularly valuable, especially for alkyl radicals with 1 to 4 carbon atoms. Alternatively, branched alkyl radicals with this number of carbon atoms are preferred.

The group of preferred linear alkyl radicals for R1 and R2 having 1 to 10 carbon atoms in the compounds of formula (i), formula (ii) and/or formula (iii) is formed from the following radicals: methyl, ethyl, n-propyl, n-butyl, n-pentyl, n-hexyl, n-heptyl, n-octyl, n-nonyl and n-decyl. Preferred linear alkyl radicals are methyl, ethyl, but n-propyl, n-butyl, n-pentyl and n-hexyl are also suitable. Particularly preferred linear alkyl radicals are methyl, ethyl, n-propyl and n-butyl.

The group of branched alkyl radicals for R1 and R2 having 1 to 10 carbon atoms in the compounds of formula (i), formula (ii) and/or formula (iii) is formed from: Isopropyl, isobutyl, sec-butyl, tert-butyl, isopentyl, tert-pentyl, iso-hexyl, tert-hexyl, iso-heptyl, iso-octyl, tert-octyl, iso-nonyl, tert-nonyl, tert-decyl and iso-decyl. Preferred branched alkyl radicals are isopropyl, isobutyl, sec-butyl and tert-butyl. Particularly preferred branched alkyl radicals are isopropyl and isobutyl.

The group of cyclic alkyl radicals for R1 and R2 having 1 to 10 carbon atoms in the compounds of formula (i), formula (ii) and/or formula (iii) is formed from: cyclopropane, cyclobutane, cyclopentane, cyclohexane, cycloheptane and cyclooctane. Preferred cyclic alkyl radicals are cyclopentane and cyclohexane.

The group of araliphatic radicals for R1 and R2 in the compounds of the formula (i), the formula (ii) and/or the formula (iii) means an alkyl radical on which one or more hydrogen atoms have been replaced by an aromatic radical. The group of araliphatic radicals in the compounds of formula (i), formula (ii) and/or formula (iii) is formed from: toluene, 2-methylfuran, 3-methylfuran, picolines, cresols, xylenes, 1-methylnaphthalene, 2-methylnaphthalene and ethylbenzene. Preferred araliphatic radical are toluene and ethylbenzene.

The group of aromatic radicals for R1 and R2 in the compounds of formula (i), formula (ii) and/or formula (iii) is formed from: pyrimidines, furan, thirane, benzene, naphthalene, phenol, pyridine and benzodiazepines. Preferred aromatic radicals are furan and benzene.

A sensory effective amount means a proportion of the substances of formula (i), formula (ii) and/or formula (iii) in the mixture sufficient to produce a fruity, pear-like odour impression. This fruity, pear-like olfactory impression is generally produced when at least 0.001 wt. % of the fragrance mixture is present by one, two or all three compounds of formula (i), formula (ii) and formula (iii).

In a preferred further modification of the present invention, the radical R1 and/or R2 in the compounds of formula (i), formula (ii) and formula (iii) in the fragrance mixture described above are each independently a C1 to C4 radical, i.e. in particular a methyl, ethyl, propyl and butyl radical. These compounds are particularly easy to make and show the most impressive odour profiles.

In an alternative preferential further modification of the present invention, the radical R1 in the compounds of formula (i), formula (ii) and formula (iii) in the fragrance mixture described above is each independently a methyl, ethyl, propyl and/or butyl radical and the radical R2 in the compounds of formula (i), formula (ii) and formula (iii) in the fragrance mixture described above is each independently a methyl radical or ethyl radical.

In a further preferred modification of the present invention, the radical R2 in the compounds of formula (i), formula (ii) and formula (iii) in the fragrance mixture described above is each independently methyl, ethyl, propyl and butyl and the radical R1 in the compounds of formula (i), formula (ii) and formula (iii) in the fragrance mixture described above is each independently methyl or ethyl.

In a second variant of the present invention, R1 and R2 in the compounds of formula (i), formula (ii) and formula (iii) in the fragrance mixture described above are each the same radicals. This simplifies production.

In a third variant of the present invention, the radicals R1 and R2 in the compounds of formula (i), formula (ii) and formula (iii) in the fragrance mixture described are each independently selected from the group consisting of: linear or branched methyl, ethyl, propyl, and butyl alkyl radicals. Especially the linear alkyl radicals and shorter branched alkyl radicals are suitable to fit into the odour-binding pockets.

In a preferred further modification of the present invention, the radicals R1 and R2 in the compounds of formula (i), formula (ii) and formula (iii) in the fragrance mixture described above are each independently methyl, ethyl, propyl and butyl.

In further preferred modifiction of the present invention, the radicals R1 and R2 in the compounds of formula (i), formula (ii) and formula (iii) in the fragrance mixture described above are each independently methyl and propyl radicals.

In a fourth variant, the invention concerns a fragrance mixture containing a sensory effective amount of one, two or all three compounds from the group formed by:

(i) (E)-2-methyl-but-2-endicarboxylic acid diethyl ester, (ii) (Z)-2-methyl-but-2-endicarboxylic acid diethyl ester, and (iii) 2-methylenebutanedicarboxylic acid diethyl ester.

These three compounds (i), (ii) and (iii) each represent the most preferred variants of the inventive formulae of the fragrance mixture, but the methyl esters or propyl esters are also favourable. The combination of ethyl ester, methyl ester and/or propyl ester is also possible.

FRAGRANCES: In the fragrances of the inventions present, the substance (E)-2-methyl-but-2-endicarboxylic acid diethyl ester of formula (I) is

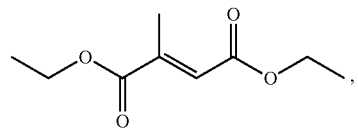

which is also known as mesaconic acid diethyl ester, is of particular importance for the invention and is already known as such from literature. Please refer to the following citations: Advanced Synthesis & Catalysis, 2012, 354 (14-15), 2859-2864; Organic Letters, 2008; 10(21), 4815-4818; Organic & Biomolecular Chemistry, 2010, 8(19), 4444-4450; Journal of American Chemical Society, 2005, 127 (15), 5518-5527; Tetrahedrone Letters, 1996, 37(5), 629-632; Tetrahedrone Letters, 1983, 39(9), 1475-1485; Journal of American Chemical Society, 2015, 137(26), 8556-8563; Organic Letters, 2011; 13(7), 1884-1887; Australian Journal of Chemistry, 1984, 37(2), 417-424; Tetrahedron Letters, 1981, 22(5), 381-384; Synthetic Communications, 1977, 7(6), 375-382; Helvetica Chimica Acta, 1974, 57(3), 856-863.

In the following, the two terms (E)-2-methyl-but-2-endicarboxylic acid diethyl ester and mesaconic acid diethyl ester are used synonymously. The sensory properties of this compound and in particular its suitability as a fragrance with a special intense pear note were not known until now. That use of that compound as a fragrance is therefore also the subject of that invention.

The two compounds of formula (ii) and formula (iii) are citracononic acid diethyl esters and itaconic acid diethyl esters, which are usually obtained together with the mesaconic acid diethyl ester as an isomeric mixture during preparation. Particularly preferred for compound (ii) is the (Z)-2-methyl-but-2-endicarboxylic acid diethyl ester and for compound (iii) the 2-methylenebutanedicarboxylic acid diethyl esters which are a preferred compound mixture with the mesaconic acid diethyl ester (E)-2-methyl-but-2-endicarboxylic acid diethyl ester. The use of these compounds individually or in combination with mesaconic acid diethyl esters as fragrances or mixtures of fragrances is also provided in accordance with the invention.

Preferred are isomer mixtures which contain the compound of formula (i), preferably (E)-2-methyl-but-2-endicarboxylic acid diethyl ester, in amounts of at least 50 to 100 wt. %, in particular about 70 to about 90 wt. % and particularly preferably about 75 to 85 wt. %.

In a fifth preferred modification of the present invention, the compound of formula (i), based on the sum of the compounds of formula (i), formula (ii) and formula (iii), is present in the fragrance mixture in an amount of 50 to 100 wt. %. This also applies to the particularly preferred compounds of the respective diethyl esters. After the invention also mesaconic acid diethyl ester is preferred in at least 98.0% but above all also in 100.0% purity. This fragrance mixture with pure or almost pure mesaconic acid diethyl ester shows a particularly strong odour with a pear note.

In a preferred variant of the invention, the relation between the compound of formula (i) relative to the sum of the two compounds of formula (ii) and of formula (iii) in the fragrance mixture is at least 8 (compound of formula (i)) to 1 (sum of the two compounds of formula (ii) and of formula (iii)), more preferably there is a ratio of 9:1 or a higher portion of formula (i). These ratios also apply to the compound mixture of mesaconic acid diethyl ester to citraconic acid diethyl ester and itaconic acid diethyl ester. Higher proportions of mesaconic acid esters produce a stronger pear scent.

In particular, it was found, that the isomeric mixture of (i), (ii) and (iii) in general and the mesaconic acid esters of the compound (i), in particular the mesaconic acid diethyl ester, are particularly excellent for imparting, modifying and/or enhancing a pear-like fragrance. The fact that the compounds have such an expressive scent is surprising as it differs from known substances with similar structures in the olfactory properties described above. Fumaric acid diethyl ester (II), for example, also has a butenedicarboxylic acid structure, but is described as almost odourless: (Source: Safety Data Sheet Fumaric acid diethyl ester, Merck):

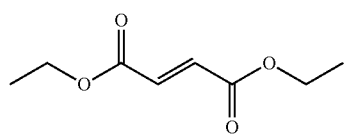

(II)

Odourally similar compounds, however, such as the 2,4-ethyl decadienoate (III) have completely different structures (cf: H. Surburg, J. Panten, Common Fragrance and Flavor Materials, 6th ed., Wiley-VCH, Weinheim, 2016, p. 25):

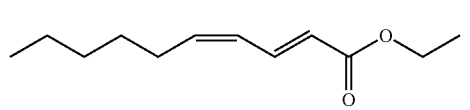

(III)

These substances also prove to be significantly weaker in terms of odour intensity and adhesion.

In addition to the special olfactory advantages, the excellent material properties, such as solubility in common cosmetic solvents, compatibility with other components of such products and the toxicological harmlessness of the compound should also be mentioned, which underscore the special suitability of the invention-based compound for the aforementioned purposes. A further advantage over conventional fragrances with similar odour profiles (e.g. Formula III) is its very favourable availability and production.

In a sixth preferred modification of the present invention, the compounds of formula (i), formula (ii) and/or formula (iii) are together contained in an amount of 0.001 to 99.999 wt. %, relative to the fragrance mixture.

Even more preferably, the compounds of formula (i), formula (ii) and/or formula (iii) are together present in an amount of 0.05 to 50 wt. %, based on the fragrance mixture. This also applies to the particularly preferred compounds of the respective diethyl esters.

In an alternatively preferred embodiment of the present invention, the compounds of formula (i), formula (ii) and/or formula (iii), based on the perfume mixture, are contained in a combined amount of 1 to 30 wt. %.

In a particularly preferred embodiment of the present invention, the mixtures may contain the compounds of formula (i), formula (ii) and/or formula (iii) in general, or the (E)-2-methyl-but-2-endicarboxylic acid diethyl ester alone, respectively said mesaconic acid diethyl ester in admixture with citracononic acid diethyl ester and itaconic acid diethyl ester in particular, in a sensory effective amount of from 0.001 to about 99.999 wt. %, preferably in an amount of from about 0.01 to about 90 wt. %, preferably in an amount of from about 0.05 to about 50 wt. %, and more preferably in an amount of from about 0.5 to about 25 wt. %. The sum of 100 wt. % is then usually made up by the other fragrances and, if appropriate, solvents and/or preservatives in the case of fragrance mixtures. Depending on the application, other additives may also be added.

Fragrances: The fragrance mixtures according to the invention necessarily contain a further fragrance, i.e. at least two fragrance components, or consist of the isomer mixture of the compounds of the formula (i), the formula (ii) and/or the formula (iii), and in particular (E)-2-methyl-but-2-endicarboxylic acid diethyl ester in a sensory effective amount with at least one further fragrance. Usually fragrances are not used in binary or ternary mixtures, but as components of sophisticated complex mixtures, which may contain 10, 20, 50, 100 or more fragrances in sometimes very small quantities to give a particularly round odour profile. In this sense, the present mixtures of the invention are to be understood, namely as a mixture of the compounds of formula (i), formula (ii) and/or formula (iii) with one, two, three, four, five, ten, preferably even a much higher number of fragrances.

In a seventh modification of the present invention, the fragrance mixture described contains any number of other fragrances selected from the group formed by: (1) hydrocarbons; (2) aliphatic alcohols; (3) aliphatic aldehydes and their acetals; (4) aliphatic ketones and their oximes; (5) aliphatic sulfur-containing compounds; (6) aliphatic nitriles; (7) esters of aliphatic carboxylic acids; (8) acyclic terpene alcohols; (9) acyclic terpene aldehydes and ketones; (10) cyclicterpene alcohols; (11) cyclicterpene aldehydes and ketones; (12) cyclic alcohols; (13) cycloaliphatic alcohols; (14) cyclic and cycloaliphatic ethers; (15) cyclic and macrocyclic ketones; (16) cycloaliphatic aldehydes; (17) cycloaliphatic ketones; (18) esters of cyclic alcohols; (19) esters of cycloaliphatic alcohols; (20) esters of cycloaliphatic carboxylic acids; (21) araliphatic alcohols; (22) esters of araliphatic alcohols and aliphatic carboxylic acids; (23) araliphatic ethers; (24) aromatic and araliphatic aldehydes; (25) aromatic and araliphatic ketones; (26) aromatic and araliphatic carboxylic acids and their esters; (27) nitrogen-containing aromatic compounds; (28) phenols, phenyl ethers and phenyl esters; (29) heterocyclic compounds; (30) lactones; and their mixtures.

The selection of fragrances is very comprehensive; corresponding substances which can be advantageously combined with mesaconic acid diethyl esters can be found, for example, in "S. Arctander, Perfume and Flavor Chemicals, Vol. I and II, Montclair, N. J., 1969, Selbstverlag" or "H. Surburg and J. Panten, Common Fragrance and Flavor Materials, 6th ed., Wiley-VCH, Weinheim, 2016". The details are set out below:

Extracts from natural raw materials: This group stands for essential oils, concretes, absolutes, resins, resinoids, balsams, tinctures, such as ambergris tincture; amyris oil; Angelica seed oil; Angelica root oil; Anise oil; valerian oil; basil oil; tree moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill herb oil; dill seed oil; eau de brouts-absolute; oakmoss-absolute; elemi oil; tarragon oil; eucalyptus citriodora oil; eucalyptus oil; fennel oil; spruce needle oil; galbanum oil; galbanum resinin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot seed oil; cascarilla oil; pine needle oil; crisped mint oil; caraway oil; labdanum oil; labdanum absolute; labdanum resin; lavandin absolute; lavandin oil; lavender absolute; lavender oil; lemongrass oil; lovage oil; lime oil distilled; pressed lime oil; linaloe oil; ILitsea cubeba oil; laurel leaf oil; mace oil; marjoram oil; mandarin oil; massoia bark oil; mimosa absolute; musk seed oil; musk tincture; muscatel sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rosewood oil; rose oil; rosemary oil; Dalmatian sage oil; Spanish sage oil; sandalwood oil; celery seed oil; spike lavender oil; star anise oil; styrax oil; marigold oil; fir needle oil; tea-tree oil; turpentine oil; thyme oil; tolu balsam; tonka absolute; tuberose absolute; vanilla extract; violet leaf absolute; verbena oil; vetiver oil; juniper berry oil; wine yeast oil; wormwood oil; wintergreen oil; ylang oil; ysop oil; civet absolute; cinnamon leaf oil; cinnamon bark oil and fractions thereof, or ingredients isolated from it.

Individual fragrances: Individual fragrances can be divided into a number of classes, namely:

Hydrocarbons, such as 3-carene; α-pinene; β-pinene; α-terpinene; γ-terpinene; p-cymene; bisabolenes; camphenes; caryophyllene; cedrenes; farnesene; limonene; longifolen; myrcene; ocimene; valence; (E,Z)-1,3,5-undecatriene; styrene; diphenylmethane;

Aliphatic alcohols such as hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; A mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxy-octan-2-ol; 9-decenol; 10-undecenol; 4-methyl-3-decen-5-ol;

Aliphatic aldehydes and their acetals, e.g. hexanal; heptanal; octanal; nonanal; decanal; undecanal; dodecanal; tridecanal; 2-methyloctanal; 2-methyl-nonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undeca-dienal; heptanal diethylacetal; 1,1-dimethoxy-2,2,5-trimethyl-4-hexene; citronellyloxyacetaldehyde; 1-(1-methoxy-propoxy)-(E/Z)-3-hexene;

Aliphatic ketones and their oximes such as 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

Aliphatic sulfur-containing compounds such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

Aliphatic nitriles such as 2-nonenoic acid nitrile; 2-undecenoic acid nitrile; 2-tridecene acid nitrile; 3,12-tridecadienoic acid nitrile; 3,7-dimethyl-2,6-octadienoic acid nitrile; 3,7-dimethyl-6-octenoic acid nitrile;

Esters of aliphatic carboxylic acids such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; Hexyl crotonate; ethyl isovalerianate; ethyl 2-methyl pentanoate; ethyl hexanoate; allyl hexanoate; ethyl heptanoate; allyl heptanoate; ethyl octanoate; Ethyl-(E,Z)-2,4-decadienoate; methyl-2-octinate; methyl-2-noninate; allyl-2-isoamyloxy-acetate; methyl-3,7-dimethyl-2,6-octadienoate; 4-methyl-2-pentyl crotonate;

Acyclic terpene alcohols such as citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerates, pentanoates, hexanoates, crotonates, tiglinates and 3-methyl-2-butenoates;

Acyclic terpene aldehydes and ketones such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

Cyclic terpene alcohols such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerianates, pentanoates, hexanoates, crotonates, tiglinates and 3-methyl-2-butenoates;

Cyclic terpene aldehydes and ketones such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

Cyclic alcohols such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethes such as cineole; cedryl methyl ether; cyclododecyl methyl ether; 1,1-dimethoxycyclododecane; (ethoxymethoxy)cyclododecane; alpha-cedrenepoxide; 3a,6,6,9a-Tetramethyldodecahydronaphtho[2,1-b]furan; 3a-Ethyl-6,6,9a-trimethyldodecahydronaphtho[2,1-b]furan; 1,5,9-Trimethyl-13-oxabicyclo[10.1.0]tri-deca-4,8-dien; rose oxide; 2-(2,4-Dimethyl-3-cyclohexen-1-yl)-5-methyl-5-(1-methylpropyl)-1,3-dioxane;

Cyclic and macrocyclic ketones such as 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

Cycloaliphatic aldehydes to which we refer 2,4-dimethyl-3-cyclohexencarbaldehyde; 2-methyl-4-(2,2,6-trimethyl-cyclohexen-1-yl)-2-butenal; 4-(4-Hydroxy-4-methylpentyl)-3-cyclohexencarbaldehyde; 4-(4-Methyl-3-penten-1-yl)-3-cyclohexencarbaldehyde;

Cycloaliphatic ketones such as 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethyl ketone; methyl-2,6,10-trimethyl-2,5,9-cyclododecatrienyl ketone; tert-butyl-(2,4-dimethyl-3-cyclohexen-1-yl)ketone;

Esters of cyclic alcohols such as 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

Esters of cycloaliphatic alcohols such as 1-cyclohexylethylcrotonate;

Esters of cycloaliphatic carboxylic acids such as allyl-3-cyclohexylpropionate; allylcyclohexyloxyacetate; cis- and trans-methyldihydrojasmonate; cis- and trans-methyljasmonate; methyl-2-hexyl-3-oxocyclopentanecarboxylate; ethyl-2-ethyl-6,6-dimethyl-2-cyclohexenecarboxylate; ethyl-2,3,6,6-tetramethyl-2-cyclohexene carboxylate; ethyl-2-methyl-1,3-dioxolan-2-acetate;

Araliphatic alcohols such as benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids, such as benzyl acetate; benzyl propionate; benzyl isobutyrate; benzyl isovalerianate; 2-phenylethyl acetate; 2-phenyl ethyl propionate; 2-phenyl ethyl isobutyrate; 2-phenyl ethyl isovalerianate; 1-phenyl ethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

Araliphatic ethers such as 2-phenylethylmethyl ether; 2-phenylethylisoamyl ether; 2-phenylethyl-1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes such as benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamic aldehyde; alpha-butylcinnamic aldehyde; alpha-amyl cinnamic aldehyde; alpha-hexyl cinnamic aldehyde; 3-methyl-5-phenylpentanal; 4-methoxybenzaldehyde; 4-hydroxy-3-methoxybenzaldehyde; 4-Hydroxy-3-ethoxybenzaldehyde; 3,4-methylenedioxybenzaldehyde; 3,4-dimethoxybenzaldehyde; 2-methyl-3-(4-methoxy-phenyl)propanal; 2-methyl-3-(4-methylenedioxyphenyl)propanal;

Aromatic and araliphatic ketones such as acetophenone; 4-methylacetophenone; 4-methoxyacetophenone; 4-tert-butyl-1,1-dimethyl-4-indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetone naphthone;

Aromatic und araliphatic carboxylic acids and their esters such as benzoic acid; phenylacetic acid; methyl benzoate; ethyl benzoate; hexyl benzoate; benzyl-benzoate; methylphenyl acetate; ethylphenyl acetate; geranylphenyl acetate; phenylethyl-phenyl acetate; methyl cinnmate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylaet; Bbnzyl salicylate; phenylethyl salicylate; methyl-2,4-dihydroxy-3,6-dimethylbenzoate; ethyl-3-phenyl glycidate; ethyl-3-methyl-3-phenyl glycidate;

Nitrogen-containing aromatic compounds such as 2,4,6-trinitro-1,3-dimethyl-5-tert-butylbenzene; 3,5-dinitro-2,6-dimethyl-4-tert-butylacetophenone; cinnamic acid nitrile; 3-methyl-5-phenyl-2-pentenitrile; 3-methyl-5-phenylpentanoic acid nitrile; methylanthranilate; methy-N-methylanthranilate; Schiff's bases of methylanthranilate with 7-hydroxy-3,7-dimethyloctanal, 2-methyl-3-(4-tert-butylphenyl) propanal or 2,4-dimethyl-3-cyclohexene carbaldehyde; 6-isopropylquinoline; 6-isobutylquinoline; 6-sec-butylquinoline; 2-(3-phenylpropyl)pyridine; indole; skatol; 2-methoxy-3-isopropylpyrazine; 2-isobutyl-3-methoxypyrazine;

Phenols, phenyl ethers und phenyl esters such as estragole; anethole; eugenol; eugenylmethyl ether; isoeugenol; isoeugenylmethyl ether; thymol; carvacrol; diphenyl ether; beta-naphthylmethyl ether; beta-naphthylethyl ether; beta-naphthylisobutyl ether; 1,4-dimethoxybenzene; eugenyl acetate; 2-methoxy-4-methylphenol; 2-ethoxy-5-(1-propenyl)phenol; p-cresylphenyl acetate;

Heterocyclic compounds such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

Lactones such as 1,4-octanolide; 3-methyl-1,4-octanolide; 1,4-nonanolide; 1,4-decaneolide; 8-decene-1,4-olide; 1,4-undecanolide; 1,4-dodecanolide; 1,5-decanolide; 1,5-dodecanolide; 1,5-methyl-1,4-decanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; coumarin; 2,3-dihydrocoumarin; octahydrocoumarin;

and any mixtures thereof.

Application Forms

An eighth aspect of the present invention concerns perfume oils, cosmetic agents, application agents or washing and cleaning agents containing the inventive fragrance mixture described.

An application agent is understood to mean all the agents mentioned herein which do not fall under the group of perfume oils, cosmetic agents or washing and cleaning agents.

After a ninth further modification of the invention, these agents contain the inventive fragrance mixture in quantities of 0.05 to 5 wt. %, based on the agent. The invention therefore concerns both perfume oils, cosmetic agents, application agents and washing and cleaning agents, including perfumed or scented products, which contain the compounds of formula (i), formula (ii) and/or formula (iii) in general, or (E)-2-methyl-but-2-endicarboxylic acid diethyl ester, respectively, the mesaconic acid diethyl ester in a mixture with citraconic acid diethyl ester and itaconic acid diethyl ester in particular, or a corresponding fragrance mixture as described, in amounts of about 0.05 to about 5 wt. %, based on the agent, preferably in amounts of about 0.1 to about 3 wt. % and in particular about 0.5 to about 2 wt. %.

Fragrance mixtures and perfume oils which contain the compounds of formula (i), formula (ii) and/or formula (iii), or preferably (E)-2-methyl-but-2-endicarboxylic acid diethyl ester, or the mixture of mesaconic acid diethyl ester, citraconic acid diethyl ester and itaconic acid diethyl ester, can be used for perfumes in liquid form, undiluted or diluted with a solvent. Suitable solvents include ethanol, isopropyl alcohol, diethylene glycol monoethyl ether, glycerol, propylene glycol, 1,2-butylene glycol, dipropylene glycol, diethyl phthalate, triethyl citrate, isopropyl myristate, etc.

These fragrance mixtures may contain up to 90 wt. %, preferably about 5 to about 70 wt. %, in particular about 10 to about 50 wt. % and especially preferably about 15 to about 25 wt. % of said solvents.

For some applications it is also advantageous to use perfume oils (fragrance mixtures) containing compounds of formula (i), formula (ii) and/or formula (iii), or preferably (E)-2-methyl-but-2-endicarboxylic diethyl ester, or the mixture of mesaconic acid diethyl ester, citraconic acid diethyl ester and itaconic acid diethyl ester adsorbed on a carrier which ensures both a fine distribution of the fragrances in the product and a controlled release during application. Such carriers may be porous inorganic materials such as light sulphate, silica gels, zeolites, gypsums, clays, clay granules, gas concrete, etc. or organic materials such as wood, cellulose-based materials, sugar or plastics such as PVC, polyvinyl acetates or polyurethanes.

For other applications it is advantageous to use the perfume oils or fragrance mixtures of the invention microencapsulated, spray-dried, as an inclusion complex or as an extrusion product and to add them in this form to the (preliminary) product to be perfumed.

In some cases, the properties of such modified perfume oils or fragrance mixtures are further optimized by so-called "coating" with suitable materials with a view to a more targeted release of fragrance, for which wax-like plastics such as polyvinyl alcohol are preferably used.

The microencapsulation of the perfume oils or fragrance mixtures of the invention can, for example, be achieved by the so-called coacervation process using capsule materials such as polyurethane-like substances or soft gelatine. Spray-dried perfume oils can, for example, be produced by spray-drying an emulsion or dispersion containing the perfume oil, using modified starches, proteins, dextrin and vegetable gums as carriers. Inclusion complexes can be prepared e.g. by adding dispersions of the perfume oil and cyclodextrins or urea derivatives to a suitable solvent, e.g. water. Extrusion products may be obtained by fusing the perfume oils with a suitable waxy substance and by extrusion followed by solidification, if necessary in a suitable solvent, e.g. isopropyl alcohol.

Cosmetic Agents and Body Care Products

In addition to the compounds of the formula (i), the formula (ii) and/or the formula (iii), or preferably (E)-2-methyl-but-2-endicarboxylic acid diethyl ester, or the mixture of mesaconic acid diethyl ester, citraconic acid diethyl ester and itaconic acid diethyl ester, the cosmetic agents and body care products according to the invention can also be formulated as follows the fragrance mixtures containing these compounds or mixtures contain other typical auxiliaries and additives, such as the mild surfactants listed below, oil bodies, emulsifiers, pearlescent waxes, consistency enhancers, thickeners, superfatting agents, stabilizers, polymers, silicone compounds, fats, waxes, lecithins, phospholipids, UV light protection factors, humectants, biogenic active ingredients, antioxidants, deodorants, antiperspirants, anti-dandruff agents, film-forming agents, swelling agents, insect repellents, self-tanning agents, tyrosine inhibitors (depigmentation agents), hydrotropes, solubilizers, preservatives, perfume oils, dyes and the like. The terms "cosmetic agents", "body care products" and "perfumed articles" are used synonymously with one another and only presuppose that the products all contain a sensory effective amount of the compounds of formula (i), formula (ii) and/or formula (iii) or preferably (E)-2-methyl-but-2-endicarboxylic acid diethyl ester, or the mixture of mesaconic acid diethyl ester, citraconic acid diethyl ester and itaconic acid diethyl ester, or of a perfume mixture containing such diesters. Preferred additives are listed below.

Surfactants: As surface-active substances, anionic, nonionic, cationic and/or amphoteric or zwitterionic surfactants may be contained, the proportion of which in the agents is usually about 1 to 70, preferably 5 to 50 and in particular 10 to 30 wt. %. Typical examples of anionic surfactants are soaps, alkylbenzene sulphonates, alkane sulphonates, olefin sulphonates, alkyl ether sulphonates, glycerol ether sulphonates, α-methyl ester sulphonates and sulphofatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulfosuccinamates, sulfotriglycerides, amide soaps, ether carboxylic acids and their salts, fatty acid isothionates, fatty acid arcosinates, fatty acid taurides, N-acylamino acids, such as acyl lactylates, acyl tartrates, acyl glutamates and acylaspartates, alkyl oligoglucoside sulfates, protein fatty acid condensates (in particular vegetable products based on wheat) and alkyl (ether) phosphates. If the anionic surfactants contain polyglycol ether chains, these may have a conventional, but preferably narrowed homologous distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular vegetable products based on wheat), polyol fatty acid esters, sugar esters, sorbitan esters, polysorbates and amine oxides. If the non-ionic surfactants contain polyglycol ether chains, these may have a conventional, but preferably narrowed homologous distribution. Typical examples of cationic surfactants are quaternary ammonium compounds, such as dimethyl distearyl ammonium chloride, and esterquats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. The surfactants mentioned are exclusively known compounds. Typical examples of particularly suitable mild, i.e. particularly skin-compatible surfactants are fatty alcohol polyglycol ether sulfates, monoglyceride sulfates, mono- and/or dialkyl sulfosuccinates, fatty acid rice thionates, fatty acid arcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter preferably based on wheat proteins.

Oil body: For example, Guerbet alcohols based on fatty alcohols with 6 to 18, preferably 8 to 10 carbon atoms, esters of linear $C_6$-$C_{22}$ fatty acids with linear or branched $C_6$-$C_{22}$ fatty alcohols, or esters of branched $C_6$-$C_{13}$ carboxylic acids with linear or branched $C_6$-$C_{22}$ fatty alcohols, such as myristyl myristate, myristyl palmitate, myristyl stearate, myristyl isostearate, myristyloleate, myristylbehenate, myristylerucate, cetyl myristate, cetyl palmitate, cetyl stearate, cetyl isostearate, cetyl oleate, cetyl behenate, cetylerucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition, esters of linear $C_6$-$C_{22}$ fatty acids with branched alcohols, in particular 2-ethylhexanol, esters of $C_{18}$-$C_{38}$ alkylhydroxycarboxylic acids with linear or branched $C_6$-$C_{22}$ fatty alcohols, in particular dioctyl malates, esters of linear and/or branched fatty acids with polyhydric alcohols (such as e.g. propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as dicaprylyl carbonates (Cetiol® CC), Guerbet carbonates based on fatty alcohols having from 6 to 18, preferably from 8 to 10 C atoms, esters of benzoic acid with linear and/or branched $C_6$-$C_{22}$ alcohols (e.g. Finsolv® TN), linear or branched, symmetrical or asymmetrical dialkyl ethers having from 6 to 22 carbon atoms per alkyl group, such as e.g. dicaprylyl ether (Cetiol® OE), ring opening products of epoxidized fatty acid esters with polyols, silicone oils (cyclomethicones, silicon-methicone types etc.) and/or aliphatic or naphthenic hydrocarbons such as squalane, squalene or dialkylcyclohexanes.

Emulsifiers: For example, non-ionic surfactants from at least one of the following groups can be used as emulsifiers:

Addition products of 2 to 30 mol ethylene oxide and/or 0 to 5 mol propylene oxide to linear fatty alcohols having 8 to 22 carbon atoms, to fatty acids having 12 to 22 carbon atoms, to alkylphenols having 8 to 15 carbon atoms in the alkyl group and to alkylamines having 8 to 22 carbon atoms in the alkyl radical;

Alkyl and/or alkenyl oligoglycosides having 8 to 22 carbon atoms in the alk(en)yl radical and ethoxylated analogues thereof;

Addition products of 1 to 15 mol ethylene oxide to ricinus oil and/or hardened ricinus oil;

Addition products of 15 to 60 mol ethylene oxide to ricinus oil and/or hardened ricinus oil;

Partial esters of glycerol and/or sorbitan with unsaturated, linear or saturated, branched fatty acids having 12 to 22 carbon atoms and/or hydroxycarboxylic acids having 3 to 18 carbon atoms and their adducts with 1 to 30 mol of ethylene oxide;

Partial esters of polyglycerol (average degree of self condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) and polyglucosides (e.g.B. cellulose) with saturated and/or unsaturated, linear or branched fatty acids having 12 to 22 carbon atoms and/or hydroxycarboxylic acids having 3 to 18 carbon atoms and their adducts with 1 to 30 mol of ethylene oxide;

Mixed esters of pentaerythritol, fatty acids, citric acid and fatty alcohol and/or mixed ester of fatty acids having 6 to 22 carbon atoms, methyl glucose and polyols, preferably glycerol or polyglycerol.

Mono-, di- and trialkylphosphates as well as mono-, di- and/or tri-PEG-alkylphosphates and their salts;

Wool wax alcohols;

Polysiloxane-polyalkyl polyether copolymers or corresponding derivatives;

Block copolymers e.g. polyethylene glycol-30 dipolyhydroxystearate;

Polymer emulsifiers, e.g. Pemulen types (TR-1, TR-2) from Goodrich or Cosmedia® SP from Cognis;

Polyalkylene glycols and

Glycerin carbonate.

Particularly suitable emulsifiers are explained in more detail below:

Alkoxylates: The addition products of ethylene oxide and/or propylene oxide to fatty alcohols, fatty acids, alkylphenols or ricinus oil are known commercially available products. These are homologous mixtures whose average degree of alkoxylation corresponds to the ratio of the quantities of ethylene oxide and/or propylene oxide and substrate with which the addition reaction is carried out. C12/18 fatty acid mono- and diesters of addition products of ethylene oxide to glycerol are known as re-fattening agents for cosmetic preparations.

Alkyl and/or alkenyl oligoglycoside: Alkyl and/or alkenyl oligoglycosides, their preparation and use are state of the art. They are produced in particular by reacting glucose or oligosaccharides with primary alcohols having 8 to 18 carbon atoms. With respect to the glycoside group, both monoglycosides, in which a cyclic sugar group is glycosidically bound to the fatty alcohol, and oligomeric glycosides having a degree of oligomerization up to preferably about 8 are suitable. The degree of oligomerisation is a statistical mean value based on a homologue distribution usual for such technical products.

Partial glycerides: Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid diglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citron diglyceride, malic acid monoglyceride, malic acid diglyceride and their technical mixtures, which may contain small amounts of triglyceride from the manufacturing process. Addition products of 1 to 30, preferably 5 to 10 mol ethylene oxide to the partial glycerides mentioned are also suitable.

Sorbitan esters: The sorbitan esters used are sorbitan monoisostearate, sorbitan sesquiisostearate, sorbitan diisostearate, sorbitan triisostearate, sorbitan monooleate, sorbitan sesquioleate and sorbitan dioleate, sorbitan trioleate, sorbitan monoerucate, sorbitan sesquierucate, sorbitan dianthucate, sorbitan trioerucate, sorbitan monoricinoleate, sorbitan sesquiricinoleate, sorbitandiricinoleate, sorbitan triicinoleate, sorbitan monohydroxystearate, sorbitan sesquihydroxystearate, sorbitan dihydroxystearate, sorbitan trihydroxystearate, Sorbitan monotarate, sorbitan sesqui tartrate, sorbitan ditartrate, sorbitan ditartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and their technical mixtures. Also suitable are addition products of 1 to 30, preferably 5 to 10 mol ethylene oxide to the sorbitan esters mentioned.

Polyglycerol ester: Typical examples of suitable polyglycerol esters are polyglyceryl-2 dipolyhydroxystearates (Dehymuls® PGPH), polyglycerol-3 diisostearates (Lameform® TGI), polyglyceryl-4 isostearates (Isolan® GI 34), polyglyceryl-3 oleates, diisostearoyl polyglyceryl-3 diisostearates (Isolan® PDI), polyglyceryl-3 methylglucose distearates (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and their mixtures. Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, optionally reacted with 1 to 30 mol ethylene oxide.

Anionic emulsifiers: Typical anionic emulsifiers are aliphatic fatty acids with 12 to 22 carbon atoms, such as palmitic acid, stearic acid or behenic acid, and dicarboxylic acids with 12 to 22 carbon atoms, such as azelaic acid or sebacic acid.

Amphoteric and cationic emulsifiers: Furthermore, zwitterionic surfactants can be used as emulsifiers. Zwitterionic surfactants are surface-active compounds that have at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example the cocosalkyldimethylammonium glycinate, N-acylaminopropyl-N,N-dimethyl ammonium glycinate, for example the cocosacylaminopropyldimethyl ammonium glycinate, and 2-alkyl-3-carboxylmethyl-3-hydroxyethyl-imidazolines each with 8 to 18 C-atoms in the alkyl or acyl group as well as the cocosacylaminoethyl-hydroxyethylcarboxymethyl glycinate. The fatty acid amide derivative known as cocamidopropyl betaine (CTFA) is particularly preferred. Ampholytic surfactants are also suitable emulsifiers. Ampholytic surfactants are surface-active compounds which, in addition to a $C_{8/18}$-alkyl or acyl group in the molecule contain at least one free amino group and at least one —COOH— or —SO$_3$H-group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are N-cocosalkylaminopropionate, cocosacylaminoethylaminopropionate and $C_{12/18}$-acylsarcosine. Finally, cationic surfactants can also be considered as emulsifiers, whereby those of the esterquat type, preferably methylquaternized difatty acid triethanolamine ester salts, are particularly preferred.

Fats and waxes: Typical examples of fats are glycerides, i.e. solid or liquid vegetable or animal products, which essentially consist of mixed glycerol esters of higher fatty acids, as waxes come natural waxes, e.g. candelilla wax, carnauba wax, Japan wax, esparto grass wax, cork wax, guaruma wax, rice germ oil wax, sugar cane wax, ouricury wax, montan wax, beeswax, shellac wax, spermaceti wax, lanolin (wool wax), rust fat, ceresin, ozokerite (earth wax), petrolatum, paraffin wax, microwaxes; chemically modified waxes (hard waxes), such as montan ester waxes, sasol waxes, hydrogenated jojoba waxes and synthetic waxes such as polyalkylene waxes and polyethylene glycol waxes in question. In addition to fats, fat-like substances such as lecithins and phospholipids can also be used as additives. Lecithins are those glycero-phospholipids which are formed from fatty acids, glycerol, phosphoric acid and choline by esterification. Lecithins are therefore often referred to as phosphatidylcholines (PC) in the scientific community. Examples of natural lecithins are cephalins, also known as phosphatidic acids, which are derivatives of 1,2-diacyl-sn-glycerol-3-phosphoric acids. By contrast, phospholipids are usually understood to be mono- and preferably diesters of phosphoric acid with glycerine (glycerine phosphates), which are generally classified as fats. Sphingosines and sphingolipids are also possible.

Pearlescent waxes: Pearlescent waxes may be used, for example: Alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols having 6 to 22 carbon atoms, especially long-chain esters of tartaric acid; fatty substances, such as fatty alcohols, fatty ketones, fatty aldehydes, fatty ethers and fatty carbonates, which in total have at least 24 carbon atoms, in particular lauron and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Coolants: Coolants are compounds that create a feeling of cold on the skin. As a rule, these are menthol compounds which—in addition to the basic menthol structure itself—are for example selected from the group consisting of menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomenthyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849) and the menthane-carboxylic acid esters and amides WS-3, WS-4, WS-5, WS-12, WS-14 and WS-30 and mixtures thereof. FEMA stands for "Flavor and Extracts Manufacturers Association" and GRAS is defined as "Generally Regarded As Safe". A FEMA GRAS designation means that the substance thus labelled is tested according to the standard method and considered toxicologically harmless.

A first important representative of these substances is the monomenthyl succinate (FEMA GRAS 3810). Both succinate and analog monomenthyl glutarate (FEMA GRAS 4006) are important representatives of monomenthyl esters based on di- and polycarboxylic acids:

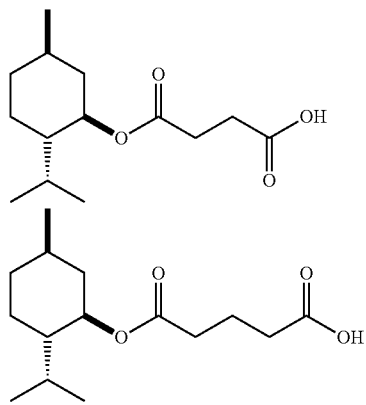

Examples of applications of these substances can be found in the publications WO 2003 043431 (Unilever) or EP 1332772 A1 (IFF).

The next important group of menthol compounds preferred in the sense of the invention includes carbonate esters of menthol and polyols, such as glycols, glycerol or carbohydrates, such as menthol ethylene glycol carbonates (FEMA GRAS 3805=Frescolat® MGC), menthol propylene glycol carbonates (FEMA GRAS 3784=Frescolat® MPC), menthol 2-methyl-1,2-propanediol carbonates (FEMA GRAS 3849) or the corresponding sugar derivatives. The menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA, are also preferred. menthone glyceryl acetal/ketal and menthyl lactate as well as menthol ethylene glycol carbonate and menthol propylene glycol Ccarbonate, which the applicant markets under the names Frescolat® MGA, Frescolat® ML, Frecolat® MGC and Frescolat® MPC, have proven to be particularly advantageous among these substances.

In the 70s of the last century, menthol compounds were developed for the first time which have a C—C bond in the 3-position and of which a number of representatives can also be used. These substances are generally referred to as WS types. The basic body is a menthol derivative in which the hydroxyl group is replaced by a carboxyl group (WS-1). All other WS types are derived from this structure, such as the preferred species WS-3, WS-4, WS-5, WS-12, WS-14 and WS-30.

Consistency enhancers and thickeners: Consistency enhancers are primarily fatty alcohols or hydroxy fatty alcohols with 12 to 22 and preferably 16 to 18 carbon atoms and also partial glycerides, fatty acids or hydroxy fatty acids. A combination of these substances with alkyl oligoglucosides and/or fatty acid N-methylglucamides of the same chain length and/or polyglycerol poly-12-hydroxystearates is preferred. Suitable thickeners include aerosil types (hydrophilic silicas), polysaccharides, in particular xanthan gum, guar guar, agar-agar, alginates and tyloses, carboxymethylcellulose and hydroxyethyl- and hydroxypropylcellulose, as well as higher molecular weight polyethylene glycol mono- and diesters of fatty acids, polyacrylates, (e.g.B. Carbopoles® and Pemulen types by Goodrich; Synthalenes® by Sigma; Keltrol types by Kelco; Sepigel types by Seppic; Salcare types by Allied Colloids), polyacrylamides, polymers, polyvinyl alcohol and polyvinylpyrrolidone. Bentonites such as Bentone® Gel VS-5PC (Rheox), a mixture of cyclopentasiloxane, disteardimonium hectorite and propylene carbonate, have also proven to be particularly effective. Other possible surfactants include ethoxylated fatty acid glycerides, esters of fatty acids with polyols such as pentaerythritol or trimethylolpropane, fatty alcohol ethoxylates with narrowed homologous distribution or alkyl oligoglucosides, and electrolytes such as sodium chloride and ammonium chloride.

Superfatting agents and stabilizers: Substances such as lanolin and lecithin as well as polyethoxylated or acylated lanolin and lecithin derivatives, polyol fatty acid esters, monoglycerides and fatty acid alkanolamides can be used as superfatting agents, the latter also serving as foam stabilizers.

Metal salts of fatty acids such as magnesium, aluminium and/or zinc stearate or ricinoleate can be used as stabilizers.

Polymers: Suitable cationic polymers are, for example, cationic cellulose derivatives such as quaternized hydroxyethylcellulose which is available from Amerchol under the name Polymer JR 400®, cationic starch, copolymers of diallylammonium salts and acrylamides, quaternized vinylpyrrolidone/vinylimidazole polymers such as Luviquat® (BASF), condensation products of polyglycols and amines, quaternized collagen polypeptides, such as lauryldimonium hydroxypropyl hydrolyzed collagen (Lamequat®L/Grünau), quaternized wheat polypeptides, polyethyleneimine, cationic silicone polymers, such as amodimethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), Polyaminopolyamides and crosslinked water-soluble polymers thereof, cationic chitin derivatives such as quaternized chitosan, optionally microcrystalline distributed, condensation products of dihalogenoalkylene, such as Dibromobutane with bisdialkylamines, such as bis-dimethylamino-1,3-propane, cationic guar gum, such as Jaguar® CBS, Jaguar® C-17, Jaguar® C-16 from Celanese, quaternized ammonium salt polymers, such as Mirapol® A-15, Mirapol® AD-1, Mirapol® AZ-1 from Miranol.

Anionic, zwitterionic, amphoteric and non-ionic polymers include vinyl acetate/crotonic acid copolymers, vinyl pyrrolidone/vinyl acrylate copolymers, vinyl acetate/butyl maleate/isobornyl acrylate copolymers, methyl vinyl ether/ maleic acid anhydride copolymers and their esters, uncrosslinked polyacrylic acids crosslinked with polyols, acrylamidopropyltrimethyl ammonium chloride/acrylate copolymers, octylacrylamide/methyl methacrylate/tert-butylaminoethylmethacrylate/2-hydroxypropylmethacrylate copolymers, polyvinylpyrrolidone, vinylpyrrolidone/vinyl acetate copolymers, vinylpyrrolidone/dimethylaminoethylmethacrylate/vinylcaprolactam terpolymers and optionally derivatised cellulose ethers and silicones.

Silicone compounds: Suitable silicone compounds are, for example, dimethylpolysiloxanes, methylphenylpolysiloxanes, cyclic silicones as well as amino, fatty acid, alcohol, polyether, epoxy, fluorine, glycoside and/or alkyl-modified silicone compounds, which may be liquid or resinous at room temperature. Simethicones, which are mixtures of dimethicones with an average chain length of 200 to 300 dimethylsiloxane units and hydrogenated silicates, are also suitable.

UV light protection factors: UV light protection factors include, for example, organic substances (light protection filters) which are liquid or crystalline at room temperature and are capable of absorbing ultraviolet rays and releasing the absorbed energy in the form of longer-waved radiation, e.g. heat. UV light protection factors are usually present in quantities of 0.1 to 5 and preferably 0.2 to 1 wt. %. UVB filters can be oil soluble or water soluble. Oil-soluble substances to be mentioned are for example:

3-benzylidenecamphor or 3-benzylidennorcamphor and its derivatives, e.g. 3-(4-methylbenzylidene)camphor;

4-Aminobenzoic acid derivatives, preferably 4-(dimethylamino)benzoic acid-2-ethylhexyl ester, 4-(dimethylamino)benzoic acid-2-octyl ester and 4-(dimethylamino)benzoic acid amyl ester;

Esters of cinnamic acid, preferably 4-methoxy cinnamic acid 2-ethylhexyl esters, 4-methoxy cinnamic acid propyl esters, 4-methoxy cinnamic acid isoamyl esters 2-cyano-3,3-phenyl cinnamic acid 2-ethylhexyl esters (octocrylenes);

Esters of salicylic acid, preferably salicylic acid 2-ethylhexyl ester, salicylic acid 4-iso-propylbenzyl ester, salicylic acid homomenthyl ester;

Benzophenone derivatives, preferably 2-hydroxy-4-methoxybenzophenone, 2-hydroxy-4-methoxy-4'-methylbenzophenone, 2,2'-dihydroxy-4-methoxybenzophenone;

Esters of benzalmalonic acid, preferably 4-methoxybenzmalonic acid di-2-ethylhexyl esters;

Triazine derivatives such as 2,4,6-trianilino-(p-carbo-2'-ethyl-1'-hexyloxy)-1,3,5-triazine and octyl triazone or dioctyl butamido triazone (Uvasorb® HEB);

Propane-1,3-diones, such as 1-(4-tert-butylphenyl)-3-(4-methoxyphenyl)propane-1,3-dione;

Ketotricyclo(5.2.1.0)decane derivatives.

Suitable water-soluble substances are:

2-Phenylbenzimidazole-5-sulfonic acid and its alkali metal, alkaline earth metal, ammonium, alkylammonium, alkanolammonium and glucammonium salts;

1H-Benzimidazole-4,6-disulfonic Acid, 2,2'-(1,4-phenylene)bis-, disodium salt (Neo Heliopan® AP)

Sulfonic acid derivatives of benzophenones, preferably 2-hydroxy-4-methoxybenzo-phenone-5-sulfonic acid and salts thereof;

Sulfonic acid derivatives of 3-benzylidenecamphor such as 4-(2-oxo-3-bornylidenemethyl)benzenesulfonic acid and 2-methyl-5-(2-oxo-3-bornylidene)sulfonic acid and salts thereof.

Typical UV-A filters are benzoylmethane derivatives, such as 1-(4'-tert-butylphenyl)-3-(4'-methoxyphenyl)propane-1,3-dione, 4-tert-Butyl-4'-methoxydibenzoylmethane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione and enamine compounds. The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-cyano-3,3-phenyl cinnamic acid 2-ethylhexyl ester (Octocrylene) in combination with esters of cinnamic acid, preferably 4-methoxy cinnamic acid 2-ethylhexyl ester and/or 4-methoxy cinnamic acid propyl ester and/or 4-methoxy cinnamic acid isoamyl ester. Such combinations are advantageously combined with water-soluble filters such as 2-phenylbenzimidazole-5-sulfonic acid and its alkali, alkaline earth, ammonium, alkylammonium, alkanolammonium and glucammonium salts.

In addition to the soluble substances mentioned above, insoluble light protection pigments, i.e. finely dispersed metal oxides or salts, can also be used for this purpose. Examples of suitable metal oxides are in particular zinc oxide and titanium dioxide and also oxides of iron, zirconium, silicon, manganese, aluminium and cerium as well as their mixtures. Silicates (talc), barium sulfate or zinc stearate can be used as salts. Oxides and salts are used in the form of pigments for skin caring and skin protecting emulsions and decorative cosmetics. The mean diameter of the particles should be less than 100 nm, preferably between 5 and 50 nm and in particular between 15 and 30 nm. They may have a spherical shape, but also particles with an ellipsoidal shape or a shape differing from the spherical shape may be used. The pigments can also be surface-treated, i.e. hydrophilized or hydrophobized. Typical examples are coated titanium dioxides, such as titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul TiO$_2$ (BASF). Silicones and in particular trialkoxyoctylsilanes or simethicones can be considered as hydrophobic coating agents. So-called micro- or nanopigments are preferably used in sunscreens. Preferably micronized zinc oxide such as Z-COTE® or Z-COTE HP1® is used.

Humectant: Humectants serve to further optimize the sensory properties of the composition and to regulate the moisture content of the skin. At the same time, the low-temperature stability of the preparations in conformity with the invention is increased, particularly in the case of emulsions. The humectants are usually present in an amount of 0.1 to 15 wt. %, preferably 1 to 10 wt. %, and in particular 5 to 10 wt. %.

Suitable products according to the invention include amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexane triol, polyethylene glycols such as PEG-4, PEG-6, PEG-7, PEG-8, PEG-9, PEG-10, PEG-12, PEG-14, PEG-16, PEG-18, PEG-20), sugar and sugar derivatives (i.a. fructose, glucose, maltose, maltitol, mannitol, mannitol, inositol, sorbitol, sorbitol silane diol, sucrose, trehalose, xylose, xylitol, glucuronic acid and salts thereof), ethoxylated sorbitol (Sorbeth-6, Sorbeth-20, Sorbeth-30, Sorbeth-40), honey and hardened honey, hardened starch hydrolysates and mixtures of hardened wheat protein and PEG-20 acetate copolymer. According to the invention, glycerine, diglycerine, triglycerine and butylene glycol are preferably used as humectants.

Biogenic agents and antioxidants: Biogenic agents include tocopherol, tocopherol acetate, tocopherol palmitate, ascorbic acid, (deoxy)ribonucleic acid and their fragmentation products, β-glucans, retinol, bisabolol, allantoin, phytantriol, panthenol, AHA acids, amino acids, ceramides, pseudoceramides, essential oils, plant extracts, such as prune extract, bambara nut extract and vitamin complexes.

Antioxidants interrupt the photochemical reaction chain that is triggered when UV radiation penetrates the skin. Typical examples are amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxine, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulfoximine compounds (e.g. buthionine sulfoximines, homocysteine sulfoximine, butionine sulfones, penta-, hexa-, heptathionine sulfoximine) in very low tolerated doses (e.g. pmol to μmol/kg), furthermore (metal) chelators (e.g. α-hydroxy fatty acids, palmitic acid, phytic acid, lactoferrin), α-hydroxy acids (e.g. citric acid, lactic acid, malic acid), humic acid, bile acids, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and its derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin-A-palmitate) as well as coniferyl benzoate of benzoic resin, rutinic acid and its derivatives, α-glycosyl rutin, ferulic acid, furfurylidene glucitol, carnosine, butyl hydroxy toluene, butylhydroxyanisole, nordihydroguajac resin acid, nordihydroguajaretic acid, trihydroxybutyrophenone, uric acid and derivatives thereof, mannose and derivatives thereof, superoxide dismutase, zinc and derivatives thereof (e.g. ZnO, ZnSO$_4$) selenium and its derivatives (e.g. selenium-methionine), stilbenes and their derivatives (e.g. stilbene oxide, trans-stilbene oxide) and the derivatives (salts, esters, ethers, sugars, nucleotides, nucleosides, peptides and lipids) of these active substances which are suitable for the invention.

Deodorants and germ-inhibiting agents: Cosmetic deodorants (deodorants) counteract, mask or eliminate body odours. Body odours are caused by the action of skin bacteria on apocrine sweat, forming unpleasant smelling degradation products. Accordingly, deodorants contain active ingredients that act as germ inhibitors, enzyme inhibitors, odour absorbers or odour concealers.

Antibacterial agents: All substances effective against gram-positive bacteria are suitable as germ-inhibiting agents, e.g. 4-hydroxybenzoic acid and its salts and esters, N-(4-chlorophenyl)-N'-(3,4-dichlorophenyl)-urea, 2,4,4'-trichloro-2'-hydroxydiphenyl ether (triclosan), 4-chloro-3,5-dimethyl-phenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), salicylic acid N-alkylamides such as salicylic acid n-octylamide or salicylic acid n-decylamide.

Enzyme inhibitors: Esterase inhibitors, for example, are suitable as enzyme inhibitors. These are preferably trialkyl citrates such as trimethyl citrate, tripropyl citrate, triisopropyl citrate, tributyl citrate and in particular triethyl citrate (Hydagen® CAT). The substances inhibit enzyme activity and thus reduce odour formation. Other substances that can be considered as esterase inhibitors are sterol sulphates or phosphates, such as lanosterol, cholesterol, campesterol, stigmasterol and sitosterol sulphate or phosphate, dicarboxylic acids and their esters, such as glutaric acid, Glutaric acid monoethyl ester, glutaric acid diethyl ester, adipic acid, adipic acid monoethyl ester, adipic acid diethyl ester, malonic acid and malonic acid diethyl ester, hydroxycarboxylic acids and their esters such as citric acid, malic acid, tartaric acid or tartaric acid diethyl ester, and zinc glycinate.

Odour absorbers: Odour absorbers are substances that absorb and largely retain odour-forming compounds. They lower the partial pressure of the individual components and thus also reduce their propagation speed. It is important that perfumes remain unaffected. Odour absorbers are not effective against bacteria. They contain, for example, a complex zinc salt of ricinoleic acid as the main component or special, largely odourless fragrances known to experts as 'fixators', such as extracts of labdanum or styrax or certain abietic acid derivatives. Fragrances or perfume oils act as odour concealers which, in addition to their function as odour concealers, give the deodorants their respective scent. Perfume oils include, for example, mixtures of natural and synthetic fragrances. Natural fragrances are extracts of flowers, stems and leaves, fruits, fruit peels, roots, woods, herbs and grasses, needles and twigs as well as resins and balms. Animal raw materials, such as zibet and castoreum, are also considered. Typical synthetic fragrance compounds are products of the ester, ether, aldehyde, ketone, alcohol and hydrocarbon type. Fragrance compounds of the ester type are e.g. benzylacetate, p-tert-butylcyclohexyl acetate, linalyl acetate, phenylethyl acetate, linalyl benzoate, benzyl formate, allylcyclohexyl propionate, styrallylpropionate and benzylsalicylate. The ethers include benzylethyl ether, the aldehydes include the linear alkanals with 8 to 18 carbon atoms, citral, citronellal, citronellyloxyacetaldehyde, cyclamenaldehyde, hydroxycitronellal, lilyal and bourgeonal, the ketones include e.g. the jonones and methylcedrylketone, the alcohols anethole, citronellol, eugenol, isoeugenol, geraniol, linalool, phenylethylalcohol and terpineol, the hydrocarbons are mainly terpenes and balsams. However, it is preferable to use mixtures of different fragrances which together produce an attractive scent. Essential oils of lower volatility, which are mostly used as aroma components, are also suitable as perfume oils, e.g. sage oil, camomile oil, clove oil, melissa oil, mint oil, cinnamon leaf oil, lime blossom oil, juniper berry oil, vetiver oil, olibanum oil, galbanum oil, labdanum oil and lavandin oil. Bergamot oil, dihydromyrcenol, Lilial, Lyral, citronellol, phenylethyl alcohol, α-hexylcinnamaldehyde, geraniol, benzylacetone, cyclamenaldehyde, linalool, Boisambrene Forte, ambroxide, indole, hedione, sandelice, citric oil, tangerine oil, orange oil, allylamylglycolate are preferred, -cyclovertal, lavandin oil, muscatel sage oil, β-damascone, geraniumoil Bourbon, cyclohexylsalicylate, Vertofix Coeur, Iso-E-Super, Fixolide NP, Evernyl, Iraldein gamma, phenylacetic acid, geranylacetate, benzyl acetate, rose oxide, Romilat, Irotyl and Floramat alone or in mixtures.

Antitranspirants: Antitranspirants (antiperspirants) reduce sweating by influencing the activity of the eccrine sweat glands, thus counteracting underarm wetness and body odor. Aqueous or anhydrous formulations of antiperspirants typically contain the following ingredients:
- astringent agents,
- oil components,
- non-ionic emulsifiers,
- coemulsifiers,
- consistency enhancer,
- excipients such as thickeners or complexing agents, and/or
- non-aqueous solvents such as ethanol, propylene glycol and/or glycerol.

The most suitable astringent antiperspirant active ingredients are salts of aluminium, zirconium or zinc. Such suitable antihydrotically active substances are e.g. aluminium chloride, aluminium chlorohydrate, aluminium dichlorohydrate, aluminium sesquichlorohydrate and their complex compounds e.g. with propylene glycol-1,2. aluminium hydroxyallantoinate, aluminium chloride tartrate, aluminium zirconium trichlorohydrate, aluminium zirconium tetrachlorohydrate, aluminium zirconium pentachlorohydrate and their complex compounds e.g. with amino acids such as glycine. In addition, antiperspirants may contain small amounts of oil-soluble and water-soluble auxiliary agents. Such oil-soluble auxiliary agents may be, for example:
- anti-inflammatory, skin protecting or fragrant essential oils,
- synthetic skin-protecting active ingredients and/or
- oil-soluble perfume oils.

Common water-soluble additives are e.g. preservatives, water-soluble fragrances, pH-value adjusting agents, e.g. buffer mixtures, water-soluble thickeners, e.g. water-soluble natural or synthetic polymers such as xanthan gum, hydroxyethylcellulose, polyvinylpyrrolidone or high-molecular polyethylene oxides.

Film forming agents: Common film forming agents include chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid or its salts and similar compounds.

Anti-dandruff active ingredients: Anti-dandruff active ingredients include piroctone olamine (1-hydroxy-4-methyl-6-(2,4,4-trimythylpentyl)-2-(1H)-pyridinone monoethanolamine salt), Baypival® (Climbazole), Ketoconazol®, (4-acetyl-1-{-4-[2-(2.4-dichlorophenyl) r-2-(1H-imidazol-1-ylmethyl)-1,3-dioxylan-c-4-ylmethoxyphenyl}piperazine, Ketoconazol, Elubiol, selenium disulfide, colloidal sulfur, sulfur polyethylene glycol sorbitan monooleate, sulfur ricinole polyehtoxylate, sulfur tar distillates, salicylic acid (or in combination with hexachlorophene), undexylenic acid monoethanolamine sulfosuccinate sodium salt, Lamepon® UD (protein undecylenic acid condensate), zinc pyrithione, aluminum pyrithione and magnesium pyrithione/dipyrithione magnesium sulfate.

Swelling agents: Montmorillonite, clay minerals, Pemulen and alkyl-modified carbopol types (Goodrich) can be used as swelling agents for aqueous phases. Further suitable polymers and swelling agents can be found in the overview of R. Lochhead in Cosm. Toil. 108, 95 (1993).

Insect repellents: N,N-diethyl-m-toluamide, 1,2-pentanediol or ethyl butylacetylaminopropionate may be used as insect repellents. Dihydroxyacetone is suitable for self-tanning. Tyrosine hinbitors that prevent the formation of melanin and are used in depigmentation agents include arbutin, ferulic acid, kojic acid, coumaric acid and ascorbic acid (vitamin C).

Ingredients for oral and dental care products: Toothpastes or tooth cremes are generally understood to be gel or paste preparations of water, thickeners, humectants, abrasives or cleaning particles, surfactants, sweeteners, flavourings, deodorising agents as well as agents against oral and dental diseases. The toothpastes according to the invention can contain all common cleaning agents, such as chalk, dicalcium phosphate, insoluble sodium metaphosphate, aluminium silicates, calcium pyrophosphate, finely divided synthetic resins, silicas, aluminium oxide and aluminium oxide trihydrate.

Preferably suitable cleaning particles for the invention toothpastes are above all finely divided xerogel silicas, hydrogel silicas, precipitated silicas, aluminium oxide trihydrate and finely divided alpha-aluminium oxide or mixtures of these cleaning bodies in quantities of 15 to 40 wt. % of the toothpaste. As humectants, low molecular weight polyethylene glycols, glycerine, sorbitol or mixtures of these products in quantities of up to 50 wt. % are predominantly used. Among the known thickeners are thickening, finely divided gel silicas and hydrocolloids such as carboxymethylcellulose, hydroxyethylcellulose, hydroxypropylguar, hydroxyethyl starch, polyvinylpyrrolidone, high-molecular polyethylene glycol, plant gums such as traganth, agar-agar, carragheen moss, gum arabic, xantham gum and carboxyvinyl polymers (e.g. Carbopol® types) suitable. In addition to the mixtures of menthofuran and menthol compounds, the oral and dental care products can contain surface-active substances in particular, preferably anionic and non-ionic high-foaming surfactants, such as the substances already mentioned above, but in particular alkyl ether sulfate salts, alkyl polyglucosides and mixtures thereof.

Other common toothpaste additives are:
- Preservatives and antimicrobial substances such as methyl, ethyl or propyl p-hydroxybenzenates, sodium sorbate, sodium benzoate, bromochlorophene, phenyl salicylic acid esters, thymol and the like;
- Anti-tartaragents, e.g. organophosphates such as 1-hydroxyethane-1,1-diphosphonic acid, 1-phosphonopropane-1,2,3-tricarboxylic acid and others known e.g. from U.S. Pat. No. 3,488,419, DE 2224430 A1 and DE 2343196 A1;
- other caries-inhibiting substances such as sodium fluoride, sodium monofluorophosphate, tin fluoride;
- Sweeteners, such as saccharin sodium, sodium cyclamate, sucrose, lactose, maltose, fructose or Apartam® (L-aspartyl L-phenylalanine methyl ester), Stivia extracts or their sweetening components, in particular ribeaudiosides;
- Additional flavours such as eucalyptus oil, anise oil, fennel oil, caraway oil, methyl acetate, cinnamon aldehyde, anethole, vanillin, thymol and mixtures of these and other natural and synthetic flavours;
- Pigments such as titanium dioxide;
- Dyestuffs;
- Buffer substances such as primary, secondary or tertiary alkali phosphates or citric acid/sodium citrate;

wound healing and anti-inflammatory substances such as allantoin, urea, azulene, camomile active ingredients and acetylsalicylic acid derivatives.

A preferred formulation of the cosmetic preparations are toothpastes in the form of an aqueous, pasty dispersion containing polishing agents, humectants, viscosity regulators and optionally further customary components, and the mixture of menthofuran and menthol compounds in amounts of 0.5 to 2 wt. %.

In mouthwashes, a combination with aqueous-alcoholic solutions of various degrees of essential oils, emulsifiers, astringent and toning drug extracts, tartar inhibiting, antibacterial additives and taste correctives is easily possible. Another preferred version of the invention is a mouthwash in the form of an aqueous or aqueous-alcoholic solution containing the mixture of menthofuran and menthol compounds in amounts of 0.5 to 2 wt. %. In mouthwashes which are diluted before use, sufficient effects can be achieved with higher concentrations according to the intended dilution ratio.

Hydrotropes: Hydrotropes such as ethanol, isopropyl alcohol or polyols can also be used to improve the flow behaviour; these substances largely correspond to the carriers described above. Polyols considered here preferably have 2 to 15 carbon atoms and at least two hydroxyl groups. The polyols may also contain other functional groups, in particular amino groups, or may be modified with nitrogen. Typical examples are Glycerin;

Alkylene glycols such as ethylene glycol, diethylene glycol, propylene glycol, butylene glycol, hexylene glycol and polyethylene glycols with an average molecular weight of 100 to 1,000 Daltons;

technical oligoglycerol mixtures having a degree of self-condensation of 1.5 to 10, such as technical diglycerol mixtures having a diglycerol content of 40 to 50 wt. %;

Methyol compounds, in particular trimethylolethane, trimethylolpropane, trimethylolbutane, pentaerythritol and dipentaerythritol;

Low alkyl glucosides, in particular those with 1 to 8 carbons in the alkyl radical, such as methyl and butyl glucosides;

Sugar alcohols with 5 to 12 carbon atoms, such as sorbitol or mannitol,

Sugar with 5 to 12 carbon atoms, such as glucose or sucrose;

Amino sugar, such as glucamine;

Dialcoholamines, such as diethanolamine or 2-amino-1,3-propanediol.

Preservatives: Suitable preservatives include phenoxyethanol, formaldehyde solution, parabens, pentanediol or sorbic acid as well as the silver complexes known under the name Surfacine® and the other substance classes listed in Annex 6, Parts A and B of the Cosmetic Regulation.

Dyestuffs: The substances suitable and approved for cosmetic purposes may be used as dyestuffs, as listed, for example, in the publication "Kosmetische Färbemittel" published by the Farbstoffkommission der Deutschen Forschungsgemeinschaft, Verlag Chemie, Weinheim, 1984, p. 81-106. Examples are Cochineal Red A (C.I. 16255), Patent Blue V (C.I.42051), Indigotine (C.I.73015), Chlorophyllin (C.I.75810), Quinoline Yellow (C.I.47005), titanium dioxide (C.I.77891), Indanthrone Blue RS (C.I. 69800) and madder lake (C.I.58000). Luminol may also be contained as a luminescent dye. These dyes are usually used in concentrations of 0.001 to 0.1 wt. %, based on the total mixture.

The total amount of excipients and additives can be 1 to 50, preferably 5 to 40 wt. %, based on the agents. The preparation of the agents can be carried out by usual cold or hot processes; preferably the phase inversion temperature method is used.

Washing and Cleaning Agents

The compounds of the formula (i), the formula (ii) and/or the formula (iii), or preferably (E)-2-methyl-but-2-endicarboxylic acid diethyl ester, or the mixture of mesaconic acid diethyl ester, citracononic acid diethyl ester and itaconic acid diethyl ester or washing and cleaning agents (abbreviated as WSR agents) containing inventive perfume mixtures within the meaning of this invention may be in solid form as powders, granules, tablets or the like, but also in liquid, gel or paste form. They are preferably washing agents suitable for both manual and mechanical washing, especially of textiles. They may also be washing or cleaning agents for industrial or household use. Cleaning agents can also be used for example for cleaning hard surfaces. They may, for example, be dishwashing detergents used for the manual or automatic cleaning of dishes. They can also be common industrial or household cleaners used to clean hard surfaces such as furniture surfaces, tiles, tiles, wall and floor coverings. In addition to tableware, all other hard surfaces, especially those made of glass, ceramics, plastic or metal, can also be considered as hard surfaces in households and businesses.

WSR agents may contain other commercial components such as surfactants, builders, bleaching agents, bleach activators, thickeners, enzymes, electrolytes, pH regulators, colouring and fragrancing agents, foam inhibitors, anti-redeposition agents, optical brighteners, greying inhibitors, anti-crease agents, antimicrobial agents, preservatives, antioxidants, antistatic agents, UV adsorbers, heavy metal complexing agents and the like. These excipients are described in more detail below:

Surfactants: In addition to non-ionic surfactants, anionic, cationic, ampho and/or niotensides and branched alkyl sulphates can also be used as surfactants in the manufacture of washing or cleaning agents.

The nonionic surfactants used are preferably alkoxylated, advantageously ethoxylated, in particular primary alcohols preferably having 8 to 18 carbon atoms and an average of 1 to 12 mol of ethylene oxide (EO) per mole of alcohol, in which the alcohol radical may be methyl-branched linearly or preferably in the 2-position or may contain linear and methyl-branched radicals in the mixture as they are usually present in oxoalcohol radicals. In particular, however, alcohol ethoxylates with linear radicals of alcohols of native origin with 12 to 18 C atoms, e.g. coconut, palm, tallow fat or oleyl alcohol, and an average of 2 to 8 EO per mole of alcohol are preferred. Preferred ethoxylated alcohols include, for example, C12-14 alcohols with 3 EO, 4 EO or 7 EO, C9-11 alcohol with 7 EO, C13-5 alcohols with 3 EO, 5 EO, 7 EO or 8 EO, C12-18 alcohols with 3 EO, 5 EO or 7 EO and mixtures thereof, such as mixtures of C12-4 alcohol with 3 EO and C12-8 alcohol with 7 EO. The stated degrees of ethoxylation are statistical averages, which may be a whole or fractional number for a particular product. Preferred alcohol ethoxylates have a narrow range of homologues (narrow range ethoxylates, NRE). In addition to these non-ionic surfactants, fatty alcohols with more than 12 EO can also be used. Examples are tallow fatty alcohols with 14 EO, 25 EO, 30 EO or 40 EO. Nonionic surfactants containing EO and PO groups together in the molecule can also be used according to the invention. Block copolymers with EO-PO block units or PO-EO block units can be used, but also EO-PO-EO copolymers or PO-EO-PO copolymers. Of course, mixed alkoxylated niotensides can also be used, in which EO and PO units are statistically distributed rather than in blocks. Such products can be obtained by the simultaneous action of ethylene oxide and propylene oxide on fatty alcohols.

Alkyl polyglycosides (APG) are another class of nonionic surfactants that can be advantageously used in the manufacture of washing or cleaning agents. Usable alklypolyglycosides satisfy the general formula RO(G)Z in which R denotes a linear or branched, in particular methyl-branched, saturated or unsaturated, aliphatic radical having 8 to 22, preferably 12 to 18 carbon atoms in the 2-position and G is the symbol which stands for a glycose unit having 5 or 6 carbon atoms, preferably glucose. The degree of glycosidation z is between 1.0 and 4.0, preferably between 1.0 and 2.0 and in particular between 1.1 and 1.4.

Nonionic surfactants of the amine oxide type, such as N-coconosalkyl-N,N-dimethylamine oxide and N-tallowalkyl-N,N-dihydroxyethylamine oxide, and fatty acid alkanolamides may also be suitable for the manufacture of washing or cleaning agents. The quantity of these nonionic surfactants shall preferably not exceed that of the ethoxylated fatty alcohols, in particular not more than half thereof.

Further suitable surfactants are polyhydroxy fatty acid amides of the formula R—CO—N(R1)-[Z] in which RCO is an aliphatic acyl radical having 6 to 22 carbon atoms, R1 is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. Polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride. The group of polyhydroxy fatty acid amides also includes compounds of the formula R—CO—N(R1-O—R2)-[Z] in which R is a linear or branched alkyl or alkenyl radical having 7 to 12 carbon atoms, R1 is a linear, branched or cyclic alkyl radical or an aryl radical having 2 to 8 carbon atoms and R2 is a linear, or an aryl radical or an oxyalkyl radical having 1 to 8 carbon atoms, C1-4 alkyl or phenyl radicals being preferred and [Z] representing a linear polyhydroxyalkyl radical whose alkyl chain is substituted by at least two hydroxyl groups, or alkoxylated, preferably ethoxylated or propoxylated derivatives of this radical. [Z] is preferably obtained by reductive amination of a sugar such as glucose, fructose, maltose, lactose, galactose, mannose or xylose. The N-alkoxy or N-aryloxy-substituted compounds can then be converted into the desired polyhydroxy fatty acid amides by reaction with fatty acid methyl esters in the presence of an alkoxide as catalyst.

The content of nonionic surfactants in the liquid washing and cleaning agents is preferably 5 to 30 wt. %, preferably 7 to 20 wt. % and in particular 9 to 15 wt. %, based in each case on the total agent.

As anionic surfactants, for example, those of the sulfonate and sulfate type are used. The surfactants of the sulfonate type used are preferably C9-3-alkylbenzene sulfonates, olefin sulfonates, i.e. mixtures of alkene and hydroxyalkane sulfonates and disulfonates such as those obtained from C12-8-monoolefins having terminal or internal double bonds by sulfonation with gaseous sulfur trioxide and subsequent alkaline or acid hydrolysis of the sulfonation products. Alkane sulfonates obtained from C12-8 alkanes, for example by sulfochlorination or sulfoxidation with subsequent hydrolysis or neutralization, are also suitable. The esters of alpha-sulfofatty acids (ester sulfonates), for example the alpha-sulfonated methyl esters of hydrogenated coconut, palm kernel or tallow fatty acids, are also suitable.

Sulfonation products of unsaturated fatty acids, such as oleic acid, are also suitable in small quantities, preferably in quantities not exceeding about 2 to 3 wt. %. In particular, alpha-sulfofatty acid alkyl esters are preferred which have an alkyl chain with no more than 4 C atoms in the ester group, for example methyl ester, ethyl ester, propyl ester and butyl ester. The methyl esters of alpha-sulfofatty acids (MES), but also their saponified disalts, are used with particular advantage.

Other anionic surfactants that can be considered are fatty acid derivatives of amino acids such as N-methyltaurine (taurides) and/or N-methylglycine (sarcosides). In particular, sarcosides and sarcosinates are preferred, especially sarcosinates of higher and possibly monounsaturated or polyunsaturated fatty acids such as oleyl sarcosinate.

Other suitable anionic surfactants are sulfonated fatty acid glycerol esters. Fatty acid glycerol esters are the mono-, di- and triesters and their mixtures as obtained in the preparation by esterification of a monoglycerol with 1 to 3 mol fatty acid or in the transesterification of triglycerides with 0.3 to 2 mol glycerol. Preferred sulfonated fatty acid glycerol esters are the sulfonated products of saturated fatty acids with 6 to 22 carbon atoms, such as caproic acid, caprylic acid, capric acid, myristic acid, lauric acid, palmitic acid, stearic acid or behenic acid.

As alk(en)yl sulfates, the alkali and in particular the sodium salts of the sulfuric acid semi-esters of the C12-C18 fatty alcohols, for example coconut fatty alcohol, tallow fatty alcohol, lauryl, myristyl, cetyl or stearyl alcohol or the C10-C20 oxo alcohols and those semi-esters of secondary alcohols of these chain lengths are preferred. Alk(en)ylsulfates of the above chain length which contain a synthetic straight-chain alkyl radical prepared on a petrochemical basis and which have an analogous degradation behaviour to the adequate compounds based on fatty-chemical raw materials are also preferred. C12-C16 alkyl sulfates and C12-C15 alkyl sulfates as well as C14-C15 alkyl sulfates are preferred for washing purposes. 2,3-alkyl sulfates, which can be obtained as commercial products of Shell Oil Company under the name DAN(R), are also suitable anionic surfactants.

The sulfuric acid monoesters of straight-chain or branched C7-21 alcohols ethoxylated with 1 to 6 moles of ethylene oxide, such as 2-methyl-branched C9-11 alcohols with an average of 3.5 moles of ethylene oxide (EO) or C12-18 fatty alcohols with 1 to 4 EO, are also suitable. Due to their high foaming behaviour, they are only used in cleaning agents in relatively small quantities, for example in quantities of 1 to 5 wt. %.

Other suitable anionic surfactants are also the salts of alkylsulfosuccinic acid, also known as sulfosuccinates or sulfosuccinic acid esters, which are monoesters and/or diesters of sulfosuccinic acid with alcohols, preferably fatty alcohols and in particular ethoxylated fatty alcohols. Preferred sulfosuccinates contain C8-18 fatty alcohol radicals or mixtures thereof. In particular, preferred sulfosuccinates contain fatty alcohol radicals derived from ethoxylated fatty alcohols, which in themselves are non-ionic surfactants (see description below). Sulfosuccinates, whose fatty alcohol radicals are derived from ethoxylated fatty alcohols with narrowed homologue distribution, are particularly preferred. It is also possible to use alk(en)yl succinic acid with preferably 8 to 18 carbon atoms in the alk(en)yl chain or salts thereof.

Especially preferred anionic surfactants are soaps. Suitable are saturated and unsaturated fatty acid soaps, such as the salts of lauric acid, myristic acid, palmitic acid, stearic acid, (hydrogenated) erucic acid and behenic acid as well as soap mixtures derived from natural fatty acids, such as coconut, palm kernel, olive oil or tallow fatty acids.

Anionic surfactants, including soaps, may be in the form of their sodium, potassium or ammonium salts and soluble salts of organic bases such as mono-, di- or triethanolamine. Anionic surfactants are preferably present in the form of their sodium or potassium salts, in particular in the form of sodium salts.

The content of anionic surfactants in preferred liquid washing and cleaning agents is 1 to 30 wt. %, preferably 4 to 25 wt. % and in particular 5 to 22 wt. %, based on the total agent. It is particularly preferred that the quantity of fatty acid soap be at least 2 wt. % and particularly preferred at least 3% by weight and particularly preferred at least 4 wt. %.

So-called Gemini surfactants can be considered as further surfactants for the production of the invention-based washing or cleaning agents. In general, this refers to compounds that have two hydrophilic groups and two hydrophobic groups per molecule. These groups are usually separated from each other by a so-called "spacer". This spacer is usually a carbon chain that should be long enough for the hydrophilic groups to have sufficient spacing to act independently. Such surfactants are generally characterized by an unusually low critical micelle concentration and the ability to greatly reduce the surface tension of the water. In exceptional cases, however, the term Gemini surfactant is understood to mean not only dimeric but also trimeric surfactants.

Gemini surfactants for the manufacture of washing or cleaning agents are, for example, sulphated hydroxy mixed ethers according to the German patent application DE-A-43 21 022 or dimeral alcohol bis- and trimeral alcohol tris-sulphates and ether sulphates according to the German patent application DE-A-195 03 061. End-group sealed dimeric and trimeric mixed ethers according to the German patent application DE-A-195 13 391 are characterized in particular by their bi- and multifunctionality. The surfactants mentioned above have good wetting properties and are low-foaming, so that they are particularly suitable for use in mechanical washing or cleaning processes.

From an application point of view, mixtures of anionic and non-ionic surfactants are preferred. The total surfactant content of the liquid washing and cleaning agent is preferably below 40 wt. % and particularly preferably below 35 wt. %, based on the total liquid washing and cleaning agent.

Builder materials: Builder materials which may be contained in liquid washing and cleaning agents include silicates, aluminium silicates (especially zeolites), carbonates, organic co-builders, phosphates, salts of organic di- and polycarboxylic acids as well as mixtures of these materials.

Suitable crystalline layered sodium silicates have the general formula $NaMSi_xO_{2x+1}*H_2O$, where M is sodium or hydrogen, x is a number from 1.9 to 4 and y is a number from 0 to 20 and preferred values for x are 2, 3 or 4. Preferred crystalline phyllosilicates of the formula given are those in which M is sodium and x is 2 or 3. In particular, both beta- and delta-sodium disilicates $Na_2Si_2O_5*yH_2O$ are preferred.

Also applicable are amorphous sodium silicates with a modulus $Na_2O{:}SiO_2$ of 1:2 to 1:3.3, preferably of 1:2 to 1:2.8 and in particular of 1:2 to 1:2.6, which are slow-dissolving and have secondary washing properties. The dissolution delay compared to conventional amorphous sodium silicates can be caused in various ways, for example by surface treatment, compounding, compaction/compression or over-drying. In the context of this invention, the term "amorphous" is also understood to mean "X-ray amorphous". This means that the silicates in X-ray diffraction experiments do not provide sharp X-ray reflexes, as they are typical for crystalline substances, but at most one or more maxima of the scattered X-ray radiation, which have a width of several degree units of the diffraction angle. However, it can very well even lead to particularly good builder properties if the silicate particles provide faded or even narrow diffraction maxima in electron diffraction experiments. This is to be interpreted in such a way that the products have microcrystalline areas in size of 10 to several hundred nm, with values up to a maximum of 50 nm and in particular up to a maximum of 20 nm being preferred. Such so-called X-ray amorphous silicates also exhibit a dissolution delay compared to conventional water glasses. Compressed/compacted amorphous silicates, compounded amorphous silicates and overdried X-ray amorphous silicates are particularly preferred.

A suitable fine crystalline, synthetic and water-bound zeolite is preferably zeolite A and/or P. Zeolite MAP TM (commercial product of Crosfield) is especially preferred as zeolite P. However, zeolite X as well as mixtures of A, X and/or P are also suitable. Commercially available and preferably used within the scope of the present invention is, for example, a co-crystallizate of zeolite X and zeolite A (approx. 80 wt. % zeolite X), which is distributed by SASOL under the brand name VEGOBOND AX(R) and which can be described by the formula:

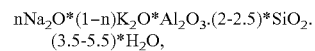
$$nNa_2O*(1-n)K_2O*Al_2O_3.(2-2.5)*SiO_2.$$
$$(3.5-5.5)*H_2O,$$

Zeolite can be used as a spray-dried powder or as an undried, stabilized suspension that is still moist from its production. If the zeolite is used as a suspension, it may contain small additions of nonionic surfactants as stabilizers, for example 1 to 3 wt. %, based on zeolite, of ethoxylated $C_{12}$-$C_{18}$ fatty alcohols with 2 to 5 ethylene oxide groups, $C_{12}$-$C_{14}$ fatty alcohols with 4 to 5 ethylene oxide groups or ethoxylated isotridecanols. Suitable zeolites have an average particle size of less than 10 μm (volume distribution; measuring method: Coulter Counter) and preferably contain 18 to 22 wt. %, in particular 20 to 22 wt. % of bound water.

Of course, it is also possible to use the generally known phosphates as builders, provided that such use should not be avoided for ecological reasons. Sodium salts of orthophosphates, pyrophosphates and especially tripolyphosphates are particularly suitable.

Suitable builders are organic co-builders, especially polycarboxylates/polycarboxylic acids, polymeric polycarboxylates, aspartic acid, polyacetals, dextrins and phosphonates.

Polymer polycarboxylates are, for example, the alkali metal salts of polyacrylic acid or polymethacrylic acid, for example those with a relative molecular weight of 500 to 70000 g/mol. The molar masses given for polymeric polycarboxylates in this publication are weight-average molar masses Mw of the respective acid form, which were basically determined by gel permeation chromatography (GPC) using a UV detector. The measurement was performed against an external polyacrylic acid standard, which provides realistic molecular weight values due to its structural relationship to the polymers investigated. These specifications differ significantly from the molecular weight specifications where polystyrenesulfonic acids are used as standard. The molecular weights measured against polystyrenesulfonic acids are generally significantly higher than the molecular weights given in this publication.

Suitable polymers are in particular polyacrylates, which preferably have a molecular mass of 2000 to 20000 g/mol. Due to their superior solubility, short-chain polyacrylates with molecular weights of 2000 to 10000 g/mol and especially 3000 to 5000 g/mol may be preferred from this group.

Also suitable are copolymeric polycarboxylates, in particular those of acrylic acid with methacrylic acid and acrylic acid or methacrylic acid with maleic acid. Copolymers of acrylic acid with maleic acid that contain 50 to 90 wt. % acrylic acid and 50 to 10 wt. % maleic acid have proven to be particularly suitable. Their relative molecular weight, relative to free acids, is generally 2,000 to 70,000 g/mol, preferably 20,000 to 50,000 g/mol and in particular 30,000 to 40,000 g/mol.

In particular, biodegradable polymers consisting of more than two different monomer units are preferred, for example those containing acrylic acid and maleic acid salts and vinyl alcohol or vinyl alcohol derivatives as monomers or acrylic acid and 2-alkylallylsulphonic acid salts and sugar derivatives as monomers.

Other preferred copolymers are those which preferably contain acrolein and acrylic acid/acrylic acid salts or acrolein and vinyl acetate as monomers.

Other preferred builders include polymeric aminodicarboxylic acids, their salts or their precursors. Polyaspartic acids or their salts and derivatives are particularly preferred, as they not only have co-builder properties but also a bleach-stabilizing effect.

Other suitable builders are polyacetals which can be obtained by reacting dialdehydes with polyolcarboxylic acids which have 5 to 7 carbon atoms and at least 3 hydroxyl groups. Preferred polyacetals are obtained from dialdehydes such as glyoxal, glutaraldehyde, terephthalaldehyde and their mixtures and from polyol carboxylic acids such as gluconic acid and/or glucoheptonic acid.

Other suitable organic builders are dextrins, for example oligomers or polymers of carbohydrates, which can be obtained by partial hydrolysis of starches. Hydrolysis can be carried out according to conventional methods, such as acid or enzyme catalysis. Preferably these are hydrolysis products with medium molecular weights in the range of 400 to 500,000 g/mol. A polysaccharide having a dextrose equivalent (DE) in the range from 0.5 to 40, in particular from 2 to 30, is preferred, wherein DE is a common measure of the reducing effect of a polysaccharide compared to dextrose which has a DE of 100. Suitable are maltodextrins with a DE between 3 and 20 and dry glucose syrups with a DE between 20 and 37 as well as so-called yellow dextrins and white dextrins with higher molecular weights in the range of 2000 to 30000 g/mol.

The oxidized derivatives of such dextrins are their reaction products with oxidizing agents which are capable of oxidizing at least one alcohol function of the saccharide ring to the carboxylic acid function. A product oxidized to C6 of the saccharide ring can be particularly advantageous.

A preferred dextrin is described in the British patent application GB 9,419,091 B1. The oxidized derivatives of such dextrins are their reaction products with oxidizing agents which are capable of oxidizing at least one alcohol function of the saccharide ring to the carboxylic acid function. Such oxidised dextrins and processes for their production are known, for example, from European patent applications EP 032202 A, EP 0427349 A, EP 0472042 A and EP 0542496 A and international patent applications WO 1992/018542 A, WO 1993/008251 A, WO 1994/028030 A, WO 1995/007303 A, WO 1995/012619 A and WO 1995/020608 A. A product oxidized to the C6 of the saccharide ring can be particularly advantageous.

Oxydisuccinates and other derivatives of disuccinates, preferably ethylenediamine disuccinate, are also suitable co-builders. Ethylenediamine-N,N'-disuccinate (EDDS) is preferably used in the form of its sodium or magnesium salts. Glycerin disuccinates and glycerin trisuccinates, as described for example in the US patent specifications U.S. Pat. Nos. 4,524,009, 4,639,325, the European patent application EP 0150930 A and the Japanese patent application JP 1993/339896 A, are also preferred in this context.

Other useful organic co-builders are, for example, acetylated hydroxycarboxylic acids or their salts, which may also be present in lactone form and which contain at least 4 carbon atoms and at least one hydroxy group as well as a maximum of two acid groups. Such co-builders are described in the international patent application WO 1995/020029 A, for example.

Phosphonates are another class of substances with co-builder properties. These are in particular hydroxyalkane or aminoalkane phosphonates. Among the hydroxyalkanephosphonates, 1-hydroxyethane-1,1-diphosphonate (HEDP) is of particular importance as a co-builder. It is preferably used as sodium salt, whereby the disodium salt reacts neutrally and the tetranate sodium salt alkaline (pH 9). The preferred aminoalkane phosphonates are ethylenediaminetetramethylenephosphonate (EDTMP), diethylenetriaminepentamethylenephosphonate (DTPMP) and their higher homologues. They are preferably used in the form of neutral reacting sodium salts, e.g. as hexanate sodium salt of EDTMP or as hepta and octa sodium salt of DTPMP. HEDP is the preferred builder from the phosphonate class. The aminoalkane phosphonates also have a pronounced heavy metal binding capacity. Accordingly, it may prefer to use its aminoalkane phosphonates, in particular DTPMP, or mixtures of these phosphonates, in particular if the washing and cleaning agents also contain bleach.

In addition, all compounds capable of forming complexes with alkaline earth ions can be used as co-builders.

Other useful organic framework substances are also polycarboxylic acids that can be used in the form of their sodium salts, whereby polycarboxylic acids are those carboxylic acids that carry more than one acid function. For example, these are citric acid, adipic acid, succinic acid, glutaric acid, malic acid, tartaric acid, maleic acid, fumaric acid, sugar acids, aminocarboxylic acids, nitrilotriacetic acid (NTA), provided that such use is not objectionable for ecological reasons, and mixtures of these. Preferred salts are the salts of polycarboxylic acids such as citric acid, adipic acid, succinic acid, glutaric acid, tartaric acid, sugar acids and mixtures of these.

The acids themselves can also be used. In addition to their builder effect, acids typically also have the property of an acidification component and thus also serve to adjust a lower and milder pH value of washing and/or cleaning agents. In particular, citric acid, succinic acid, glutaric acid, adipic acid, gluconic acid and any mixtures thereof should be mentioned.

Bleaching agents and bleaching catalysts: Among the compounds used as bleaching agents and supplying $H_2O_2$ in water, sodium perborate tetrahydrate and sodium perborate monohydrate are of particular importance. Other useful bleaching agents include sodium percarbonate, peroxypyrophosphates, citrate perhydrates as well as peracid salts or peracids providing $H_2O_2$, such as perbenzoates, peroxophthalates, diperazelaic acid, phthaloiminoperacid or diperdodecanedioic acid. In order to achieve an improved bleaching effect when washing at temperatures of 60° C. and below, bleach activators can be incorporated into the washing and cleaning agents. The bleach activators used may be compounds which, under perhydrolysis conditions, give aliphatic peroxocarboxylic acids preferably having 1 to 10 carbon atoms, in particular 2 to 4 carbon atoms, and/or optionally substituted perbenzoic acid. Substances which carry O- and/or N-acyl groups of the C atom number mentioned and/or optionally substituted benzoyl groups are suitable. Preferred are multiple acylated alkylenediamines, especially tetraacetylethylenediamine (TAED), acylated triazine derivatives, especially 1,5-diacetyl-2,4-dioxohexahydro-1,3,5-triazine (DADHT), acylated glycolurils, in particular tetraacetylglykoluril (TAGU), N-acylimides, in particular N-nonanoylsuccinimide (NOSI), acylated phenol sulfonates, in particular nonanoyl- or isonanoyloxybenzenesulfonate (n- or iso-NOBS), carboxylic anhydrides, in particular phthalic anhydride, acylated polyhydric alcohols, in particular triacetine, ethylene glycol diacetate and 2,5-diacetoxy-2,5-dihydrofuran. In addition to or in place of conventional bleach activators, bleaching catalysts can also be incorporated into textile treatment agents. These substances are bleach-reinforcing transition metal salts or transition metal complexes such as Mn, Fe, Co, Ru or Mo-Salen complexes or carbonyl complexes. Mn, Fe, Co, Ru, Mo, Ti, V and Cu complexes with nitrogen-containing tripod ligands and Co, Fe, Cu and Ru ammine complexes can also be used as bleaching catalysts.

Thickener: A liquid washing and cleaning agent may contain a thickener. The thickener may include, for example, a polyacrylate thickener, xanthan gum, gellan gum, guar gum, alginate, carrageenan, carboxymethylcellulose, bentonite, wellan gum, locust bean gum, agar-agar, tragacanth, gum arabic, pectins, polyoses, starch, dextrins, gelatin and casein. However, modified natural substances such as modified starches and celluloses, such as carboxymethyl cellulose and other cellulose ethers, hydroxyethyl and propyl cellulose as well as nuclear powder ethers, can also be used as thickeners.

Polyacryl and polymethacryl thickeners include, for example, the high molecular weight homopolymers of acrylic acid cross-linked with a polyalkenyl polyether, in particular with an allyl ether of sucrose, pentaerythritol or propylene (INCI designation according to the "International Dictionary of Cosmetic Ingredients" of "The Cosmetic, Toiletry and Fragrance Association (CTFA)": Carbomer), which are also referred to as carboxyvinyl polymers. Such polyacrylic acids are available among others from the company 3V Sigma under the trade name Polygel®, e.g. Polygel DA, and from B.F. Goodrich under the trade name Carbopol®, e.g. Carbopol 940 (molecular weight approx. 4,000,000), Carbopol 941 (molecular weight approx. 1,250,000) or Carbopol 934 (molecular weight approx. 3,000,000): (i) copolymers of two or more monomers selected from the group consisting of acrylic acid, methacrylic acid and their simple esters (INCI acrylate copolymer), preferably formed with C1-4 alkanols, such as the copolymers of methacrylic acid, butyl acrylate and methyl methacrylate (CAS denomination according to Chemical Abstracts Service: 25035-69-2) or of butyl acrylate and methyl methacrylate (CAS 25852-37-3) and which are, for example, produced by the company Rohm and Haas under the trade names Aculyn® and Acusol® and from Degussa (Goldschmidt) under the trade name Tego® Polymer, e.g. the anionic non-associative polymers Aculyn 22, Aculyn 28, Aculyn 33 (crosslinked), Acusol 810, Acusol 820, Acusol 823 and Acusol 830 (CAS 25852-37-3); (ii) crosslinked high-molecular-weight acrylic acid copolymers, such as those copolymers (crosslinked with an allyl ether of sucharose or pentaerythritol) of C10-30 alkyl acrylates with one or more monomers from the group consisting of acrylic acid, methacrylic acid and their simple esters, preferably formed with C1-4 alkanols, (INCI Acrylates/C10-30Alkyl Acrylate Crosspolymer) and which are available, for example, from the company B.F. Goodrich under the trade name Carbopol®, e.g. the hydrophobized Carbopol ETD 2623 and Carbopol 1382 (INCI acrylates/C10-30 alkyl acrylate crosspolymer) as well as Carbopol Aqua 30 (formerly Carbopol EX 473).

Another preferred polymeric thickener is xanthan gum, a microbial anionic heteropolysaccharide produced by Xanthomonascampestris and some other species under aerobic conditions and having a molecular weight of 2 to 15 million daltons. Xanthan gum is formed from a chain of beta-1,4-bound glucose (cellulose) with side chains. The structure of the subgroups consists of glucose, mannose, glucuronic acid acetate and pyruvate, with the number of pyruvate units determining the viscosity of the xanthan gum. A fatty alcohol in particular may also be used as a thickening agent. Fatty alcohols may be branched or unbranched and of native or petrochemical origin. Preferred fatty alcohols have a C chain length of 10 to 20 C atoms, preferably 12 to 18. Mixtures of different C chain lengths, such as tallow fatty alcohol or coconut fatty alcohol, are preferred. Examples are Lorol® Special (C12-14-ROH) or Lorol® Technical (C12-18-ROH) (both ex Cognis). Preferred liquid washing and cleaning agents contain 0.01 to 3 wt. % and preferably 0.1 to 1 wt. % of thickeners, based on the total agent. The amount of thickener used depends on the type of thickener and the desired degree of thickening.

Enzymes: The washing and cleaning agents may contain enzymes in encapsulated form and/or directly in the washing and cleaning agents. Enzymes that can be considered are those from the classes of hydrolases such as proteases, esterases, lipases or lipolytically active enzymes, amylases, cellulases or other glycosyl hydrolases, hemicellulase, cutinases, beta-glucanases, oxidases, peroxidases, perhydrolases and/or laccases and mixtures of the aforementioned enzymes. All these hydrolases contribute to the removal of stains such as protein-, grease- or starch-containing stains and greying in the laundry. Cellulases and other glycosylhydrolases also help to retain the colour and increase the softness of the textile by removing pilling and microfibrils. Oxireductases can also be used to bleach or inhibit dye transfer. Particularly suitable are enzymatic active substances obtained from bacterial strains or fungi such as *Bacillus subtilis, Bacillus licheniformis, Streptomyceus griseus* and Humicolainsolens. Proteases of the subtilisin type and in particular proteases derived from *Bacillus lentus* are preferably used. These are enzyme mixtures, for example from protease and amylase or protease and lipase or lipolytically acting enzymes or protease and cellulase or from cellulase and lipase or lipolytically acting enzymes or from protease, amylase and lipase or lipolytically active enzymes or protease, lipase or lipolytically active enzymes and cellulase, but in particular protease and/or lipase-containing mixtures or mixtures with lipolytically active enzymes of particular interest. Examples of such lipolytically active enzymes are the well-known cutinases. Peroxidases or oxidases have also proven to be suitable in some cases. Suitable amylases include in particular alpha-amylases, iso-amylases, pullulanases and pectinases. Cellulases used are preferably cellobiohydrolases, endoglucanases and p-glucosidases, also known as cellobiases, or mixtures of these. Since different cellulase types differ in their CMCase and avicelase activities, targeted mixtures of cellulases can be used to stop the desired activities.

The enzymes can be adsorbed on carriers to protect them against premature decomposition. The proportion of enzymes, the enzyme liquid formulation(s) or the enzyme granules directly in washing and cleaning agents can, for example, be about 0.01 to 5 wt. %, preferably 0.12 to about 2.5 wt. %.

However, it may also be preferable, for example in the case of special washing and cleaning agents for consumers with allergies, that the washing and cleaning agent does not contain any enzymes.

Electrolytes: A wide variety of salts can be used as electrolytes from the group of inorganic salts. Preferred cations are alkali and alkaline earth metals, preferred anions are halides and sulfates. From a manufacturing point of view, the use of NaCl or $MgCl_2$ in washing and cleaning agents is preferred. The proportion of electrolytes in washing and cleaning agents is usually 0.1 to 5 wt. %.

Solvents: Non-aqueous solvents which can be used in liquid washing and cleaning agents originate from the group of monohydric or polyhydric alcohols, alkanolamines or glycol ethers, for example, provided that they are miscible with water within the specified concentration range. The solvents are preferably selected from ethanol, n- or i-propanol, butanols, glycol, propane or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, Diethylene glycol ethyl ether, propylene glycol methyl, ethyl or propyl ether, dipropylene glycol monomethyl or ethyl ether, di-isopropylene glycol monomethyl or ethyl ether, methoxy, ethoxy or butoxytriglycol, 1-butoxyethoxy-2-propanol, 3-methyl-3-methoxybutanol, propylene glycol t-butyl ether and mixtures of these solvents. Non-aqueous solvents can be used in liquid washing and cleaning agents in quantities between 0.5 and 15 wt. %, but preferably below 12 wt. % and in particular below 9 wt. %.

Viscosity regulators: The viscosity of washing and cleaning agents in liquid form can be measured using standard methods (e.g. Brookfield viscometer LVT-II at 20 rpm and 20° C., spindle 3) and is preferably in the range of 500 to 5000 mPas for liquid washing agents. Preferrably liquid washing and cleaning agents have viscosities from 700 to 4000 mPas, with values between 1000 and 3000 mPas being especially preferred. The viscosity of fabric softeners is preferably 20 to 4000 mPas, with values between 40 and 2000 mPas being preferred. Especially preferred is the viscosity of fabric softeners from 40 to 1000 mPas.

pH control agents: To bring the pH value of the liquid washing and cleaning agents into the desired range, the use of pH control agents may be indicated. All known acids and alkalis can be used here unless their use is prohibited for technical or ecological reasons or for reasons of consumer protection. Usually, the quantity of these agents does not exceed 7 wt. % of the total formulation. The pH value of liquid washing and cleaning agents is preferably between 4 and 10 and preferably between 5.5 and 8.5. The pH value of liquid fabric softeners is preferably between 1 and 6 and preferably between 1.5 and 3.5.

Dyestuffs: In order to improve the aesthetic impression of textile treatment agents, they can be dyed with suitable dyestuffs. Preferred dyestuffs, the selection of which does not present any difficulty to the specialist, have a high storage stability and insensitivity to the other ingredients of washing and cleaning agents and to light, as well as no pronounced substantivity against textile fibres in order not to dye them.

Antiredeposition agents: Suitable soil release polymers, also referred to as 'antiredeposition agents', are for example non-ionic cellulose ethers such as methylcellulose and methylhydroxypropylcellulose with a methoxy group content of 15 to 30 wt. % and hydroxypropyl groups of 1 to 15 wt. %, in each case based on the nonionic cellulose ether and the polymers of phthalic acid and/or terephthalic acid known from the state of the art or of derivatives thereof, in particular polymers of ethylene terephthalates and/or polyethylene and/or polypropylene glycol terephthalates or anionically and/or nonionically modified derivatives thereof. Suitable derivatives include the sulfonated derivatives of phthalic acid and terephthalic acid polymers.

Optical brighteners: Optical brighteners (so-called "whiteners") can be added to washing and cleaning agents to eliminate greying and yellowing of the treated textile fabrics. These substances attract onto the fibre and cause a brightening and fake bleaching effect by converting invisible ultraviolet radiation into visible wavelengths of light, whereby the ultraviolet light absorbed from the sunlight is emitted as weakly bluish fluorescence and produces pure white with the yellow tone of the greyed or yellowed laundry. Suitable compounds come, for example, from the substance classes of 4,4'-diamino-2,2'-stilbendisulfonic acids (flavonic acids), 4,4'-distyryl-biphenylene, methylumbelliferones, coumarins, dihydroquinolinones, 1,3-diarylpyrazolines, naphthalic acid imides, benzoxazole, benzisoxazole and benzimidazole systems as well as pyrene derivatives substituted by heterocycles. The optical brighteners are usually used in quantities between 0 and 0.3 wt. %, based on the finished washing and cleaning agent.

Greying inhibitors: Greying inhibitors have the task of keeping the dirt detached from the fibre suspended in the liquor and thus preventing the dirt from reappearing. For this purpose, water-soluble colloids of mostly organic nature are suitable, for example glue, gelatine, salts of ether sulfonic acids of starch or cellulose or salts of acid sulfuric acid esters of cellulose or starch. Water-soluble polyamides containing acid groups are also suitable for this purpose. Furthermore, soluble starch preparations and starch products other than those mentioned above may be used, e.g. degraded starch, aldehyde starches, etc. polyvinylpyrrolidone is also useful. Cellulose ethers such as carboxymethylcellulose (Na salt), methylcellulose, hydroxyalkylcellulose and mixed ethers such as methylhydroxyethylcellulose, methylhydroxypropylcellulose, methylcarboxymethylcellulose and their mixtures in quantities of 0.1 to 5 wt. %, based on washing and cleaning agents, are preferred.

Anti-crease agents: As textile fabrics, especially those made of rayon, rayon, cotton and their blends, may tend to crease because the individual fibres are sensitive to bending, creasing, pressing and squeezing across the grain direction, washing and cleaning agents may contain synthetic anti-crease agents. These include, for example, synthetic products based on fatty acids, fatty acid esters, fatty acid amides, alkylol esters, alkylol amides or fatty alcohols, which are usually reacted with ethylene oxide, or products based on lecithin or modified phosphoric acid esters.

Antimicrobial agents: To combat micro-organisms, washing and cleaning agents may contain antimicrobial agents. Depending on the antimicrobial spectrum and mechanism of action, a distinction is made between bacteriostats and bactericides, fungistatics and fungicides, etc. Important substances from these groups include benzalkonium chlorides, alkylarylsulfonates, halogenphenols and phenolmercuriacetate, whereby these compounds can also be completely dispensed with in inventive washing and cleaning agents.

Preservatives: The inventive washing and cleaning agents invented may contain preservatives, preferably using only those with no or little skin sensitizing potential. Examples are sorbic acid and salts thereof, benzoic acid and salts thereof, salicylic acid and salts thereof, phenoxyethanol, 3-iodo-2-propynylbutylcarbamate, sodium N-(hydroxymethyl)glycinate, biphenyl-2-ol and mixtures thereof. A suitable preservative is the solvent-free, aqueous combination of diazolidinylurea, sodium benzoate and potassium sorbate (available as Euxyl® K 500ex Schülke and Mayr), which can be used in a pH range up to 7. Preservatives based on organic acids and/or their salts are particularly suitable for preserving the invention's skin-friendly washing and cleaning agents.

Antioxidants: To prevent undesirable changes in washing and cleaning agents and/or treated textile fabrics caused by exposure to oxygen and other oxidative processes, washing and cleaning agents may contain antioxidants. This compound class includes for example substituted phenols, hydroquinones, pyrocatechins and aromatic amines as well as organic sulfides, polysulfides, dithiocarbamates, phosphites, phosphonates and vitamin E.

Antistatics: Increased wearing comfort can result from the additional use of antistatic agents, which are added to the washing and cleaning agents. Antistatic agents increase the surface conductivity and thus allow an improved discharge of formed charges. Antistatic agents are usually substances with at least one hydrophilic molecular organ and give a more or less hygroscopic film on the surfaces. These mostly surface-active antistatic agents can be divided into nitrogen-containing (amines, amides, quaternary ammonium compounds), phosphorus-containing (phosphoric acid esters) and sulfur-containing (alkyl sulfonates, alkyl sulfates) antistatic agents. Lauryl (or stearyl) dimethylbenzylammonium chlorides are suitable as antistatic agents for textile fabrics or as an additive to washing and cleaning agents, whereby an additional finishing effect is achieved.

Foam inhibitors: To improve the rewettability of the treated textile fabrics and to facilitate ironing of the treated textile fabrics, silicone derivatives, for example, can be used in the textile treatment agents. These also improve the rinsing behavior of washing and cleaning agents through their foam-inhibiting properties. Preferred silicone derivatives are, for example, polydialkyl or alkylarylsiloxanes in which the alkyl groups have one to five C atoms and are completely or partially fluorinated. Preferred silicones are polydimethylsiloxanes, which may be derivatized and then aminofunctional or quaternized or have Si—OH, Si—H and/or Si—Cl bonds. The viscosities of the preferred silicones are between 100 and 100,000 mPas at 25° C., and the silicones can be used in quantities between 0.2 and 5 wt. %, based on the total washing and cleaning agent.

UV absorbers: Finally, the washing and cleaning agents can also contain UV absorbers which are applied to the treated textile fabrics and improve the lightfastness of the fibres. Compounds having these desired properties are, for example, the compounds and derivatives of benzophenone effective by non-radiative deactivation with substituents in the 2- and/or 4-position. Also suitable are substituted benzotriazoles, phenyl-substituted acrylates (cinnamic acid derivatives) in the 3-position, optionally with cyano groups in the 2-position, salicylates, organic Ni complexes and natural substances such as umbelliferone and the body's own urocanic acid.

Heavy metal complexing agents: In order to avoid the decomposition of certain ingredients of washing agents catalysed by heavy metals, substances can be used which complex heavy metals. Suitable heavy metal complexing agents are, for example, the alkali salts of ethylenediaminetetraacetic acid (EDTA) or nitrilotriacetic acid (NTA) as well as alkali metal salts of anionic polyelectrolytes such as polymaleates and polysulfonates. A preferred class of complexing agents are phosphonates, which are present in preferred textile treatment agents in quantities of 0.01 to 2.5 wt. %, preferably 0.02 to 2 wt. % and in particular 0.03 to 1.5 wt. %. These preferred compounds include in particular organophosphonates such as 1-hydroxyethane-1,1-diphosphonic acid (HEDP), aminotri(methylenephosphonic acid) (ATMP), diethylenetriaminepenta(methylenephosphonic acid) (DTPMP or DETPMP) and 2-phosphonobutane-1,2,4-tricarboxylic acid (PBS-AM), which are mostly used in the form of their ammonium or alkali metal salts.

Preparation of the compounding: The production of solid WSR agents can be carried out by the usual methods, such as tower spraying, fluid bed drying, agglomeration, powder mixing, tabletting, granulation, especially SKET granulation.

Liquid WSR agents are also produced by common and well-known methods and processes, for example by simply mixing the components in stirred vessels, where water, non-aqueous solvents and surfactants are appropriately placed and the other components are added in portions. Thus, liquid washing and cleaning agents can be produced by starting with the acidic components such as linear alkyl sulphonates, citric acid, boric acid, phosphonic acid, fatty alcohol ether sulphates, etc., and the non-ionic surfactants. The solvent component is preferably also added at this time, but can also be added at a later time. The thickening agent, for example a polyacrylate, can be added to these components. Then a base such as NaOH, KOH, triethanolamine or monoethanolamine is added followed by the fatty acid, if present. The remaining ingredients and solvents of the aqueous liquid washing and cleaning agent are then added to the mixture and the pH adjusted to approximately 8.5. Finally, the particles to be dispersed can be added and homogeneously distributed in the aqueous liquid washing and cleaning agent by mixing.

This invention concerns perfume oils or preparations perfumed or scented in this way. The invention therefore concerns both perfume oils, cosmetic agents, application agents and washing and cleaning agents, including perfumed or scented products, which contain the compounds of formula (i), formula (ii) and/or formula (iii) in general, or the (E)-2-methyl-but-2-endicarboxylic acid diethyl ester, respectively, the mesaconic acid diethyl ester in admixture with citracononic acid diethyl ester and itaconic acid diethyl ester in particular, or a corresponding perfume mixture as described, said perfume oils or agents being selected from the group consisting of: Perfume extracts, eau de parfums, eau de toilettes, shaving lotions, eau de colognes, pre-shave products, splash colognes and perfumed refreshing wipes as well as the perfuming of acidic, alkaline and neutral cleaning agents, e.g. floor cleaners, window glass cleaners, dishwashing detergents, bathroom and sanitary cleaners, scouring lotions, solid and liquid WC cleaners, powdered and foamed carpet cleaners, liquid wasching agents, powdery washing agents, laundry pretreatment agents such as bleaching agents, soaking agents and stain removers, fabric softener, washing soap, washing tablets, disinfectants, surface disinfectants and air fresheners in liquid, gel-like or on a solid carrier applied form, aerosol sprays, waxes and polishes such as furniture polishes, floor waxes, shoe polishes and body care products such as solid and liquid soaps, shower gels, shampoos, shaving soaps, shaving foams, bath oils, cosmetic emulsions of oil-in-water, water-in-oil and water-in-oil-in-water types such as skin creams and lotions, face creams and lotions, sun protection creams and lotions, aftersun creams and lotions, hand creams and lotions, foot creams and lotions, depilatory creams and lotions, aftershave creams and lotions, tanning creams and lotions, hair care products such as hair sprays, hair gels, hair lotions, hair conditioners, permanent and semi-permanent hair dyes, hair deformers such as cold waves and hair straighteners, hair tonics, hair creams and lotions, deodorants and antiperspirants such as armpit sprays, roll-ons, deodorant sticks, deocreams or decorative cosmetic products.

In particular, the invention concerns according to a tenth aspect means selected from the group that is formed from: solid and liquid soaps, shower gels, shampoos, shaving soaps, shaving foams, bath oils, cosmetic emulsions, skin creams and lotions, facial creams and lotions, sun protection creams and lotions, after-sun creams and lotions, hand creams and lotions, foot creams and lotions, depilatory creams and lotions, after-shave creams and lotions, tanning creams and lotions, hair sprays, hair gels, hair lotions, hair conditioners, permanent and semi-permanent hair dyes, hair deforming agents, hair tonics, hair creams and lotions, deodorants, underarm sprays, roll-ons, deodorant sticks, deodorant cremes and decorative cosmetic products as well as perfume extracts, eau de parfums, eau de toilettes, shaving lotions, eau de colognes, pre-shave products, splash colognes, refreshing wipes, acidic, alkaline and neutral cleaning agents, floor cleaners, window glass cleaners, dishwashing detergents, bathroom and sanitary cleaners, scouring lotions, solid and liquid WC cleaners, powdered and foamed carpet cleaners, liquid washing agents, powdery washing agents, laundry pretreatment agents, bleaching agents, soaking agents and stain removers, fabric softeners, washing soaps, washing tablets, disinfectants, surface disinfectants, air fresheners in liquid, gel-like or on a solid carrier applied form, aerosol sprays, furniture polishes, floor waxes, shoe polishes.

Manufacturing Process I

An eleventh object of the present invention concerns a process for the preparation of a mono- and/or diester of mesaconic acid comprising the following steps:
(i) reacting itaconic acid with acetic anhydride to obtain itaconic acid anhydride;
(ii) isomerization of itaconic acid anhydride to citraconic acid anhydride;
(iii) esterification of citraconic acid anhydride with an aliphatic, araliphatic or aromatic alcohol having 1 to 10 carbon atoms or diol having 1 to 5 hydroxyl groups to give a mono- and/or diester of the citraconic acid; and
(iv) rearrangement of the mono- and/or diester of the citraconic acid to a mono- and/or diester of the mesaconic acid.

The method is exemplified by the preferred production of (E)-2-methyl-but-2-endicarboxylic acid diethylester (mesaconic acid diethyl ester) or a mixture thereof with citraconic acid diethyl ester and itaconic acid diethyl ester in Scheme A below.

In the first reaction step, an itaconic acid (preferably itaconic acid diethyl ester) is generally reacted with an approximately equimolar amount of acetic anhydride to form the cyclic anhydride and release acetic acid. The reaction usually takes place at temperatures in the range of 50 to 95° C. The acetic acid is then distilled off in a vacuum.

In the second step, thermodynamically controlled isomerization of the itaconic acid anhydride to citraconic acid anhydride takes place. The reaction is preferably carried out in a solvent and requires temperatures from 200 to 250° C. Here, too, the solvent is subsequently removed.

The third step is esterification with ethanol in excess, which is carried out acid-catalyzed under reflux. Subsequently, alcohol that has not been converted is distilled off.

The last fourth step is the rearrangement of the citraconic acid ester (preferably citracononic acid diethyl ester) into the mesaconic acid (preferably diethyl ester of mesaconic acid). This reaction preferably takes place in a suitable solvent, such as MtBE, at temperatures in the range 170 to 200° C.; iodine is added to the mixture as catalyst. The solvent is then separated again by distillation.

An illustration of the implementation of the procedure from step (i) to step (iv) can be found in the examples section.

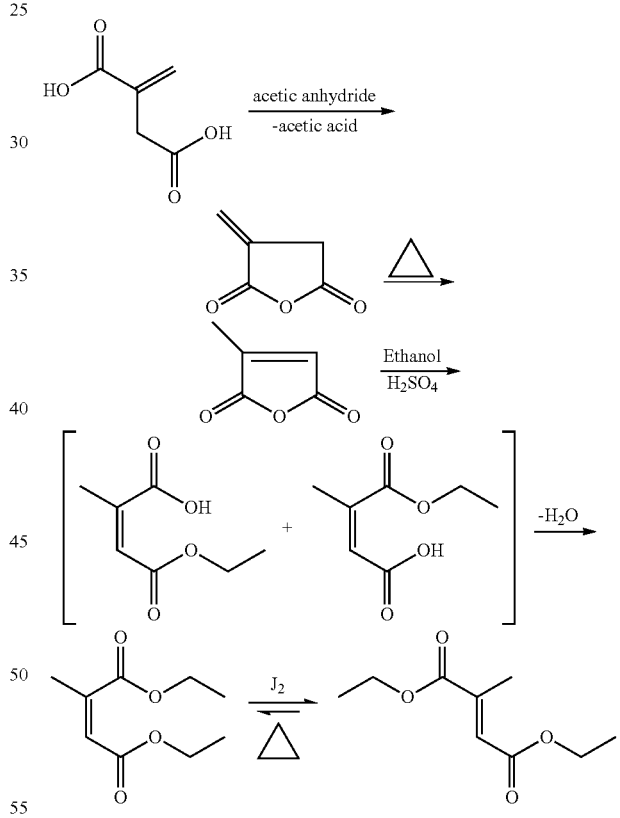

Scheme A

The process for the preparation of a mono- and/or diester of mesaconic acid is particularly preferred in a further modification of the invention, wherein in step (ii) a high-boiling solvent is used, preferably a polyalkylene glycol (PAG) having the structure: RO—[CH$_2$—C(CH$_3$)HO]n-[CH$_2$CH$_2$O]m-H.

The high-boiling solvent preferably contains solvents with a boiling point of more than 250° C., even more preferably more than 300° C. Here, polyalkylene glycol (PAG)-based products have proven their worth. Such are e.g. Synalox® 50-B SYNALOX™ 50-xB, which are known as lubricants, and are alcoholic materials containing oxyethylene and oxypropylene groups with a single terminal hydroxyl group with structure:

RO—[CH$_2$—C(CH$_3$)HO]$_n$—[CH$_2$CH$_2$O]$_m$—H

Known to be 50-50B SYNALOX: molecular weight: 1300.

In a twelfth modification of the invention, in step (ii) a solvent system comprising a high boiling point solvent, preferably a polyalkylene glycol (PAG), having a boiling point of greater than 150° C. and further comprising a co-solvent having a boiling point of between 90° C. and 120° C., preferably dioxane, is used. This system significantly increases the yield, because without the protective solvent, the distilled product tends to polymerize on a quantitative scale with larger reaction vessels on the longer distillation route. Thus, it could be shown that even with larger batches, the yield could be increased or remains high if the protective solvent has a boiling point, such that it can also be distilled with the product to prevent polymerisation of the product during distillation. The co-solvent or protective solvent is particularly preferred with a boiling point between 95° C. and 110° C., particularly preferred between 100° C. and 105° C. Dioxane is suitable.

The co-solvent can be separated after the distillation step by common processes.

Other suitable co-solvents are:

aliphatic hydrocarbons and more specifically paraffins such as in particular octane, isooctane, nonane, decane, undecane, tetradecane; aromatic hydrocarbons such as in particular toluene, xylene, ethylbenzene, diethylbenzene, trimethylbenzene, cumene, pseudocumene, petroleum fractions consisting of a mixture of alkylbenzenes, in particular fractions of the Solvesso® type, chlorinated aliphatic hydrocarbons such as 1,1,2-trichloroethane, pentachloroethane, 1-iodo-2-methylpropane, 1-chlorohexane, 1-chloro-2-ethylhexane; chlorinated aromatic hydrocarbons and special chlorobenzenes, chlorotoluenes, Ethers and more specifically aliphatic ethers such as butyl ether, isobutyl ether, ethylhexyl ether, 1-butoxy-2-methoxyethane, 1,1-diethoxybutane, amylether, isoamyl ether, dipropoxymethane; aromatic ethers such as phenyl propyl ether, mesity oxide, nitrated compounds, such as nitropropane, nitrobenzene, aliphatic, cycloaliphatic or aromatic ketones, preferably methyl ethyl ketone, methyl isobutyl ketone, diisobutyl ketone, methyl n-amyl ketone, methyl isoamyl ketone, cyclohexanone, methyl cyclohexanone, diacetone alcohol.

The co-solvents can also be used as a separate mixture.

Manufacturing Process II

A thirteenth aspect of the present invention concerns a process for the preparation of a mono- and/or diester of mesaconic acid comprising the following steps:
(i) providing a solution comprising at least one mono- and/or diester of citraconic acid and optionally a solvent;
(ii) adding iodine to the solution;
(iii) heating the iodine-containing solution to about 170 to about 200° C.; and
(iv) optionally, distillative purification of the resulting product.

Furthermore, it is preferred that the manufacturing process II is used as step (iv) in manufacturing process I. The last rearrangement step is thus carried out after manufacturing process II, as it were, following steps (i) to (iii) in manufacturing process I. The last rearrangement step is therefore carried out after steps (i) to (iii) in manufacturing process II.

In a fourteenth modification of the present invention, the mono- and/or diesters of mesaconic acid described above in Methods I and II are (E)-2-methyl-but-2-endicarboxylic acid esters, preferably (E)-2-methyl-but-2-endicarboxylic acid diethyl esters.

A preferred embodiment of the present invention therefore concerns a process for the preparation of (E)-2-methyl-but-2-endicarboxylic acid diethyl ester comprising the following steps:
(i) providing a solution comprising at least citracononic acid diethyl ester and optionally a solvent;
(ii) addition of iodine to the solution;
(iii) heating of the iodine-containing solution to about 170 to about 200° C. and
(iv) where appropriate, distillative purification of the resulting product.

Mono- and/or diesters of citraconic acid with aliphatic, araliphatic or aromatic alcohols containing 1 to 10 carbon atoms or diols containing 2 to 6 hydroxyl groups are preferably used as starting materials. In particular, mono- and diesters of citraconic acid with methanol, isopropyl alcohol, the isomeric butanols, ethylene glycol, diethylene glycol, propylene glycol, dipropylene glycol or glycerol and in particular ethanol are used. With regard to the special features of the process, reference is made to the explanations on the first manufacturing process, stage (iv), which are included here.

Uses

A fifteenth aspect of the invention concerns a process for imparting, modifying or enhancing a fruity, pear-like scent note in a fragrance mixture, perfume oil, cosmetic agents, applicator or washing and cleaning agent comprising the following steps:
(a1) providing at least one or more of the inventive compound(s) of formula (i), formula (ii) and/or formula (iii) or an inventive fragrance composition containing said compound(s) and
(a2) mixing a sensory effective amount of that substance or substances with a mixture of additional fragrances sufficient to afford a fruity, pear-like scent in the finished preparation, or (b1) providing at least one or more of the inventive compound(s) of formula (i), formula (ii) and/or formula (iii) or an inventive fragrance mixture containing said compound(s) and
(b2) mixing a sensory effective amount of that substance or substances with the perfume oil, cosmetic agent, application or washing and cleaning agent sufficient to afford a fruity, pear-like scent note in the finished preparation.

Preferably, the compound(s) of formula (i), formula (ii) and/or formula (iii) corresponding to the invention are each the (E)-2-methyl-but-2-endicarboxylic acid diethyl ester (mesaconic acid diethyl ester), citraconic acid diethyl ester and itaconic acid diethyl ester, or a mixture of (E)-2-methyl-but-2-endicarboxylic acid diethyl ester with citraconic acid diethyl ester and itaconic acid diethyl ester.

A sixteenth and seventeenth aspect of the invention concerns the use of compounds of formula (i), formula (ii) and/or formula (iii) or mixtures thereof in general, or the (E)-2-methyl-but-2-endicarboxylic acid diethyl ester alone, or mesaconic acid diethyl ester mixed with citraconic acid diethyl ester and itaconic acid diethyl ester in particular, or a corresponding fragrance mixture according the invention on the one hand:

as fragrances, and on the other hand for imparting, modifying or enhancing a fruity, pear-like scent note in a fragrance mixture, a perfume oil, cosmetic agents, application agent or washing and cleaning agent.

With regard to preferred input materials and input quantities, reference is made to the above remarks, which are included herein, so that a repetition is not necessary. The preferred compounds are those of formula (i), formula (ii) and/or formula (iii) or mixtures thereof in general. In particular, it is pointed out once again that the particularly preferred variants and further modifications of any form of the present invention each refer to mesaconic acid diethyl ester, as compound (i), respectively an isomer mixture, in particular a mixture of (E)-2-methyl-but-2-endicarboxylic acid diethyl ester with citraconic acid diethyl ester and itaconic acid diethyl ester, which contains this compound in an amount of at least 50 wt. %.

EXAMPLES

Example for Production Process 1: Preparation of mesaconic acid diethyl ester=(E)-2-methyl-but-2-ene-dicarboxylic acid diethyl ester Stage 1: Itaconic Acid Anhydride

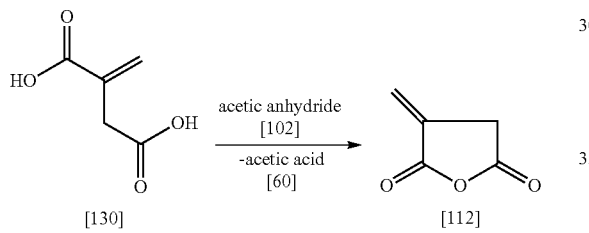

612 g (6.0 mol) of acetic anhydride were placed in a 2-litre three-necked flask with KPG stirrer, 15-Vigreux column and column head and 780 g (6.0 mol) of solid itaconic acid was added while stirring. The mixture was then slowly heated to 80° C. until the solid was dissolved and stirred for another 30 minutes at this temperature. Subsequently, approx. 680 g acetic acid was distilled off at a vacuum between 150 and 10 mbar and a sump temperature of 80 to 82° C. The acetic acid was then removed from the sample. Approx. 690 g of sump bottom product remained, the raw yield being 680 g. The raw product was used directly in stage 2.

A 5 g sample of the ester was purified by ball tube distillation and analyzed by gas chromatography and had a composition of 11 wt. % citraconic acid anhydride and 89 wt. % itaconic acid anhydride.

Stage 2: Citraconic Acid Anhydride

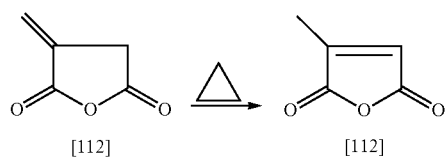

In a 2-liter three-necked flask with KPG stirrer, 15 Vigreux column and column head, 100 g of a high-boiling solvent (Synalox® 50-B) were placed in the flask and heated to 230° C. while stirring. Subsequently, 690 g of itaconic acid anhydride (crude product stage 1), dissolved in 100 g Synalox, were dosed at a vacuum of approx. 350 mbar within 4 hours. The isomerization product citraconic acid anhydride was continuously extracted with an R/D ratio of 1:1. At the end of the dosing process, the vacuum was increased to 10 mbar and a total of 630 g distillate was obtained, which corresponded to a yield of 94% over both stages. The GC purity was 99%.

Stage 3: Citric Acid Diethyl Ester

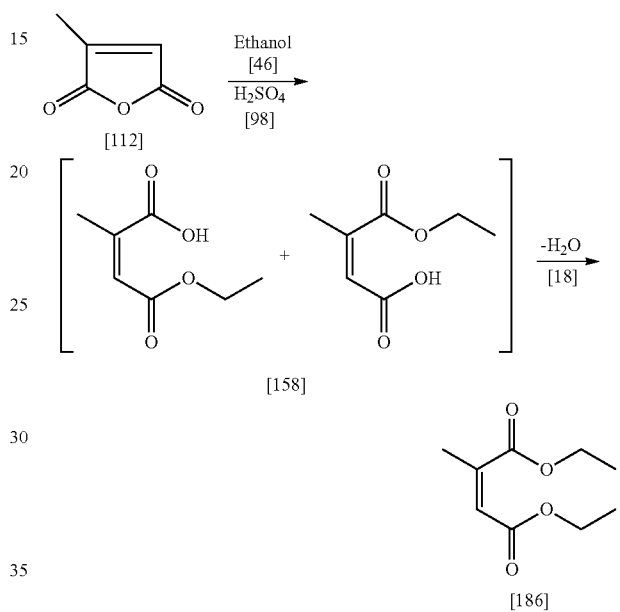

In a 2-litre three-necked flask with KPG stirrer, 15 Vigreux column and column head, 780 g ethanol was added and 630 g (5.63 mol) citraconic acid anhydride was added while stirring at room temperature. Subsequently 30 g concentrated sulphuric acid were added within 5 min and heated for 2 hours under reflux. 530 g of a mixture of ethanol/water (80/20 wt. %) were then distilled off at normal pressure and a head temperature of 86° C. (R/D 1:3, duration approx. 80 min). One sample was purified by ball tube distillation and analyzed by gas chromatography, whereby 10 wt. % citraconic acid anhydride and 89 wt. % citracononic acid diethyl ester were found.

A further 230 g ethanol was then added and again heated for 1 hour under reflux at a head temperature of 84° C. Then 170 of a mixture of ethanol/water (90/10 wt. %) were distilled off (R/D 1:3, duration approx. 40 min). One sample was processed by ball tube distillation and analyzed by gas chromatography, finding 5 wt. % citraconic acid anhydride and 95 wt. % citracononic acid diethyl ester.

Again, 140 g ethanol were added, heated for 1 hour under reflux and a mixture of 110 g ethanol/water (90/10 wt. %) was distilled off at a head temperature of 82° C. (R/D 1:3, duration approx. 25 min). A sample was processed by ball tube distillation and analyzed by gas chromatography. This revealed 2 wt. % citraconic acid anhydride and 96 wt. % citracononic acid diethyl ester.

The reaction product was then cooled to room temperature and washed with 400 g water after 400 g MTBE had been added. The organic phase was then first washed three times with saturated sodium bicarbonate solution under strong carbon dioxide development and then with 400 g of a 5 wt. % saline solution. After phase separation, a total of 1,970 g of aqueous phase (waste water fraction I, pH 6) and 1,140 g of organic phase were present.

10% of the organic phase was processed by distillation and analyzed by gas chromatography: Yield: 74 g (71% of theory); purity: 99% citracronic acid diethyl ester.

Stage 4: Mesaconic Acid Diethyl Ester

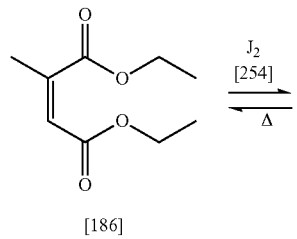
[186]

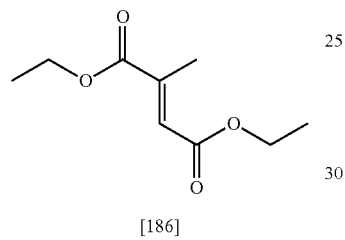
[186]

In a 2 litre three-neck flask with KPG stirrer, 15 Vigreux column and column head, 1,100 g of citraconic acid diethyl ester in MTBE (raw product stage 3) were placed and the solvent was distilled off to a sump temperature of 150° C. at 50 to 80 mbar. In this way, about 320 g of MTBE was obtained, which could be used again (see below). Then it was cooled down to approx. 80° C., aerated and mixed with 8 g (31 mmol) iodine while stirring. It was heated to 190° C. for 1 hour. One sample was purified by ball tube distillation and analyzed by gas chromatography, 72.9 wt. % mesaconic acid diethyl ester, 1.1 wt. % itaconic acid diethyl ester and 25.9 wt. % citraconic acid diethyl ester were found.

Since the proportion of the mesaconic acid ester was still below 80 wt. %, reaction vessel was heated to 190° C. for another hour. One sample was purified by ball tube distillation and analyzed by gas chromatography, and 84.6 wt. % of mesaconic acid diethyl ester, 1.4 wt. % of itaconic acid diethyl ester and 13.8 wt. % of citraconic diethyl ester were found.

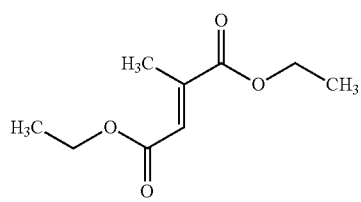

Mesaconic acid diethyl ester=(E)-2-methyl-but-2-enedicarboxylic acid-diethyl ester

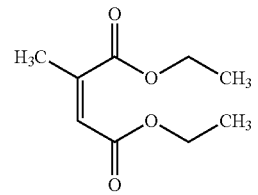

Citracononic acid diethyl ester=(Z)-2-methyl-but-2-ene-dicarboxylic acid diethyl ester

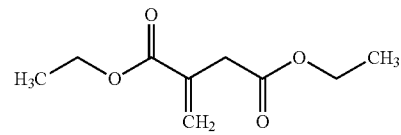

Itaconic acid diethyl ester=2-methylene-butanedicarboxylic acid diethyl ester

After cooling to about 40 to 45° C., 320 g of reused MTBE was added while stirring and it was washed four times with 300 g of a 40% w/w sodium hydrogen sulphite solution, one time with 300 g 5% w/w sodium bicarbonate solution and one time with 300 g 10% w/w sodium chloride solution, with phase separations occurring within 5 minutes. A total of about 1,800 g aqueous phase (waste water fraction II, pH 4) and about 1,000 g organic phase were obtained. The product was cleaned with a quantity of about 1,000 g using a 10 cm nudist column according to Table 1.

TABLE 1

| | Distillative Cleaning | | | | | |
|---|---|---|---|---|---|---|
| fraction | T(sump) [° C.] | T(head) [° C.] | Pressure [mbar] | R/D | Quantity [g] | analysis |
| 1 | 76-96 | 55-69 | 300 | — | 250 | MTBE |
| 2 | 96-97 | 82 | 300 | — | 8 | intermediate |
| 3 | 97-115 | 82 | | — | 707 | mesaconic acid ester (84.6%) |
| | | | | | 26 | residue |
| | | | | | 29 | cold trap |

The product either turned pink during distillation or discoloured when left standing. To decolorize the ester, 14 g activated carbon was added to the ester while stirring, stirred for 30 minutes at room temperature and then filtered. The yield was 705 g (95% of the theory).

Rearrangement Step (ii) with Solvent System

An improved process using a solvent mixture is described below.

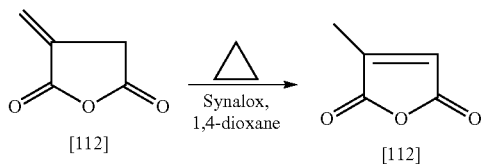

The solvent mixture Synalox plus 1,4-dioxane is used in the production of citraconic acid anhydride from itaconic acid anhydride. This offers a good yield even with larger approaches. The following implementation was applied.

The itaconic acid anhydride was placed in dioxane or obtained as a residue from step (i) (3 mol), mixed with 390 g 1,4-dioxane and filled into the dropping funnel.

After this, step (ii) is carried out in accordance with the prescription set out below.

| Implementation | Duration [h:min] | Total rec. time [h:min] | Fr. | Temp. [° C.] | Head [° C.] | Dest. [g] | Remarks |
|---|---|---|---|---|---|---|---|
| Place 300 g Synalox on top and heat up | 0:15 | 0:15 | | | | 20-230 | |
| Dos. Itaconic acid anhydride in dioxane | 2:35 | 2:50 | 2 | 230-235 | 57-135 | 686 | Vacuum (350-20 mbar) |

The product is then evaporated in a rotation evaporator (60-70° C./100-20 mbar) and 296 g (GC purity=96.6%) of the citraconic acid anhydride is obtained with a yield of 85%.

Production of Further Esters

In analogy to the above-mentioned process examples for (E)-2-methyl-but-2-enedicarboxylic acid diethyl esters, further esters were produced. In particular, the methyl, propyl and n-butyl esters of mesaconic acid were synthesized and analyzed. This resulted in a total of four compounds variants:

(E)-2-methyl-but-2-endicarboxylic acid dimethyl ester,
(E)-2-methyl-but-2-endicarboxylic acid diethyl ester,
(E)-2-methyl-but-2-endicarboxylic acid dipropyl ester,
(E)-2-methyl-but-2-endicarboxylic acid dibutyl ester.

Spectroscopic Data:

(E)-2-methyl-but-2-endicarboxylic acid dimethyl ester $^1$H-NMR (400 MHz, CDCl$_3$): δ=2.31 (d, J=1.6 Hz, 3H), 3.78 (s, 3H), 3.28 (s, 3H), 6.80 (q, J=1.6 Hz, 1H).
$^{13}$C NMR (CDCl$_3$, 101 MHz): δ=167.6 (C=O), 166.3 (C=O), 143.7 (C), 126.5 (CH), 52.6 (CH$_3$), 51.7 (CH$_3$), 14.3 (CH$_3$).
MS (70 eV): 158, 143, 127, 113, 99.

(E)-2-methyl-but-2-ene-dicarboxylic acid diethyl ester $^1$H-NMR (400 MHz, CDCl$_3$): δ=1.32 ppm (t, J=7.1 Hz, 3H), 1.33 ppm (t, J=7.1 Hz, 3H), 2.29 (d, J=1.6 Hz, 3H), 4.23 (q, J=7.1 Hz, 2H), 4.26 (q, J=7.1 Hz, 2H), 6.78 (q, 1.6 Hz, 1H).
$^{13}$C NMR (CDCl$_3$, 101 MHz): δ=167.16 (C=O), 165.97 (C=O), 143.76 (C), 126.66 (CH), 61.57 (CH$_2$), 60.62 (CH$_2$), 14.27 (CH$_3$), 14.20 (CH$_3$), 14.13 (CH$_3$).
MS (70 eV): 186, 157, 141, 113, 99.

(E)-2-methyl-but-2-endicarboxylic acid dipropyl ester $^1$H-NMR (400 MHz, CDCl$_3$): δ=0.98 (t, J=7.4 Hz, 3H), 0.98 (t, J=7.4 Hz, 3H), 1.79-1.64 (m, 4H), 2.29 (d, J=1.6 Hz, 3H), 4.13 (t, J=6.5 Hz, 2H), 4.16 (t, J=6.5 Hz, 2H), 6.79 (q, J=1.6 Hz, 1H).
$^{13}$C NMR (CDCl$_3$, 100 MHz): δ=167.3 (C), 166.1 (C), 143.7 (C), 126.7 (CH), 67.2 (CH$_2$), 66.3 (CH$_2$), 21.9 (CH$_2$), 21.6 (CH$_2$), 14.3 (CH$_3$), 10.4 (CH$_3$), 10.4 (CH$_3$).
MS (70 eV): 214, 199 185, 155, 131, 96.

(E)-2-methyl-but-2-endicarboxylic acid dibutyl ester $^1$H-NMR (400 MHz, CDCl$_3$): δ=0.95 (t, J=7.3 Hz, 3H), 0.96 (t, J=7.3 Hz, 3H), 1.47-1.36 (m, 4H), 1.72-1.61 (m, 4H), 2.29 (d, J=1.6 Hz, 3H), 4.18 (t, J=6.7 Hz, 2H), 4.20 (t, J=6.6 Hz, 2H), 6.77 (q, J=1.6 Hz, 1H).
$^{13}$C NMR (CDCl$_3$, 100 MHz): δ=167.3 (C), 166.1 (C), 143.7 (C), 126.7 (CH), 65.5 (CH$_2$), 64.6 (CH$_2$), 30.5 (CH$_2$), 30.6 (CH$_2$), 19.19 (CH$_2$), 19.18 (CH$_2$), 14.3 (CH$_3$), 13.7 (CH$_3$).
MS (70 eV): 242, 227, 213, 169, 131, 68.

Table 2 below shows the results of the GC profile and fragrance test for the esters produced. The abbreviations DD and TN stand for the terms "dry down" and "top note".

TABLE 2

| Compound structure | GC profile: DB Wax | Fragrance: |
|---|---|---|
| methyl | | |
| (E)-2-methyl-but-2-endicarboxylic acid dimethyl ester | 86% | DD: Nothing TN: anise, anethol, fruity, pineapple, green. |
| (Z)-2-methyl-but-2-endicarboxylic acid dimethyl ester | 11% | |
| 2-Methylene-butanedicarboxylic acid dimethyl ester | 3% | |
| ethyl | | |
| (E)-2-methyl-but-2-ene-dicarboxylic acid diethyl ester | 85% | DD: buttery, sugary TN: fruity, green, pear |
| (Z)-2-methyl-but-2-ene-dicarboxylic acid diethyl ester | 13.8% | |
| 2-Methylene-butanedicarboxylic acid diethyl ester | 1.4% | |

TABLE 2-continued

| Compound structure | GC profile: DB Wax | Fragrance: |
|---|---|---|
| propyl | | |
| (E)-2-methyl-but-2-endicarboxylic acid dipropyl ester | 82% | DD: same as ethyl; TN: fruity, sugary, linear, violet, |
| (Z)-2-methyl-but-2-endicarboxylic acid dipropyl ester | 9% | |
| 2-Methylene-butanedicarboxylic acid dipropyl ester | 6% | |
| n-butyl | | |
| (E)-2-methyl-but-2-endicarboxylic acid dibutyl ester | 88% | DD: same as ethyl; TN: greener than others, but weak. green, fruity |
| (Z)-2-methyl-but-2-endicarboxylic acid dibutyl ester | 3% | |
| 2-Methylene-butanedicarboxylic acid dibutyl ester | 8% | |

APPLICATION EXAMPLES

Example 1: Shower Gel

| Material | Manufacturer | INCI name | wt. % |
|---|---|---|---|
| Deionized water | | Water | 76.3 |
| Plantacare PS 10 | Cognis Germany GmbH | sodium laureth sulfates, lauryl glucosides | 20.0 |
| Dragocid Liquid | Symrise | phenoxyethanol, methylparaben, ethylparaben, butylparaben, propylparaben, isobutylparaben | 0.5 |
| Sodium chloride | | sodium chloride | 1.4 |
| Citric acid monohydrate crystalline | | citric acid | 1.3 |
| Perfume oil A1 or A2 from this example 1 | Symrise | Perfume (Fragrance) | 0.5 |

Perfume Composition for a Shower Gel

| | A1 Comparative example | A2 Example according to invention |
|---|---|---|
| HEXENAL TRANS-2 10% DPG | 5 | 5 |
| HEXENOL BETA GAMMA CIS, TRANS-3 | 1 | 1 |
| HEXENOL TRANS-2 10% DPG | 1 | 1 |
| HEXENYLACETATE CIS, TRANS-3 10% DPG | 6 | 6 |
| HEXENYLISOBUTYRATE CIS-3 10% DPG | 5 | 5 |
| VERTOCITRAL 10% DPG | 7 | 7 |
| STYROLYL ACETATE 10% DPG | 5 | 5 |
| ITAL. CITRIC OIL | 10 | 10 |
| BUTYLACETATE | 10 | 10 |
| HEXYLACETATE | 30 | 30 |
| ISOAMYLACETATE | 11 | 11 |
| JASMAPRUNATE | 40 | 40 |
| PRENYL ACETATE | 3 | 3 |
| ALDEHYDE C14 SOG | 4 | 4 |
| PYROPRUNATE | 10 | 10 |
| FRAMBINON ® 10% DPG | 5 | 5 |
| MALTOL 1% DPG | 2 | 2 |
| DIMETHYLBENZYLCARBINYLBUTYRATE | 15 | 15 |
| PURE GERANYLACETATE | 220 | 220 |
| DAMASCENONE | 2 | 2 |
| ISODAMASCON ® | 5 | 5 |
| HEDIONE | 100 | 100 |
| AGRUMEX HC | 14 | 14 |
| AMBRETTOLIDE | 1 | 1 |
| ETHYLENE BRASSYLATE | 3 | 3 |
| GLOBALIDE | 5 | 5 |
| MESACONIC ACID DIETHYL ESTER | — | 80 |
| DIPROPYLENE GLYCOL | 480 | 400 |
| | 1000 | 1000 |

Mesaconic acid diethyl ester can be easily and stably incorporated into any perfume composition and adds a natural, fruity and radiant note.

Example 2: Body Lotion

| Component | wt. % | wt. % |
|---|---|---|
| paraffin oil | 5.00 | 5.00 |
| isopropyl palmitate | 5.00 | 5.00 |
| cetyl alcohol | 2.00 | 2.00 |
| beeswax | 2.00 | 2.00 |
| Ceteareth-20 | 2.00 | 2.00 |
| PEG-20 glyceryl stearate | 1.50 | 1.50 |
| glycerin | 3.00 | 3.00 |
| phenoxyethanol | 0.50 | — |
| Parabens (mixture of methyl-, ethyl-, propyl-, butyl-, isobutylparabens) | — | 0.50 |
| Perfume oil B1 or B2 | 0.50 | 0.50 |
| water | Ad 100 | Ad 100 |

Perfume Oils for this Body Lotion

| Fragrances | Perfume oil B1 comparative | Perfume oil B2 inventive |
|---|---|---|
| NONADIENAL TRANS, CIS-2,6 5% TEC 20% DPG | 2.0 | 2.0 |
| ETHYL ACETOACETATE | 3.0 | 3.0 |
| FARENAL ® 10% DPG | 5.0 | 5.0 |
| VERTOCITRAL | 3.0 | 3.0 |
| CYCLOGALBANAT ® 10% DPG | 2.0 | 2.0 |
| STYRALYL ACETATE | 3.0 | 3.0 |
| MELONAL ® | 0.5 | 0.5 |
| DIHYDRO MYRCENOL | 15.0 | 15.0 |
| LINALYL ACETATE | 20.0 | 20.0 |
| LEMON OIL TERPENES FLAVOR WONF | 8.0 | 8.0 |
| EUCALYPTOL NAT. 10% DPG | 0.5 | 0.5 |
| HEXYL ACETATE | 1.5 | 1.5 |
| ISOAMYL ACETATE 10% DPG | 4.0 | 4.0 |
| PRENYL ACETATE 10% DPG | 4.0 | 4.0 |
| ALDEHYDE C14 SO-CALLED | 2.0 | 2.0 |
| ETHYL METHYL BUTYRATE-2 | 1.0 | 1.0 |
| ALLYL CYCLOHEXYL PROPIONATE | 2.0 | 2.0 |
| ALDEHYDE C16 SO-CALLED | 1.0 | 1.0 |
| FRAGOLANE ® | 0.5 | 0.5 |

| Fragrances | Perfume oil B1 comparative | Perfume oil B2 inventive |
|---|---|---|
| MAJANTOL ® | 25.0 | 25.0 |
| LINALOOL | 40.0 | 40.0 |
| DIMETHYL BENZYL CARBINOL | 10.0 | 10.0 |
| TERPINEOL PURE | 10.0 | 10.0 |
| PHENIRAT ® | 30.0 | 30.0 |
| CITRONELLOL 950 | 15.0 | 15.0 |
| GERANIOL 60 | 10.0 | 10.0 |
| CITRONELLYL ACETATE EXTRA | 2.0 | 2.0 |
| HEDIONE | 90.0 | 90.0 |
| HEXYL CINNAMIC ALDEHYDE ALPHA | 35.0 | 35.0 |
| HEXYL SALICYLATE | 160.0 | 160.0 |
| METHYL OCTIN CARBONATE 10% DPG | 2.0 | 2.0 |
| CALONE 1951 10% DPG | 1.0 | 1.0 |
| GALAXOLIDE 50% IN IPM | 20.0 | 20.0 |
| ANETHOLE SUPRA 21.5 CELSIUS | 2.0 | 2.0 |
| AGRUMEX HC | 15.0 | 15.0 |
| ORYCLON SPECIAL | 40.0 | 40.0 |
| MESACONIC ACID DIETHYL ESTER | — | 15.0 |
| DIPROPYLENE GLYCOL | 415.0 | 400.0 |
| | 1.000.0 | 1.000.0 |

The addition of mesaconic acid diethyl ester (MSDEE) to the fragrance composition results in a fresher, fruity note. In addition, the top note becomes more radiant and the end note more nourishing.

Example 3: Fabric Softener

| Material | Manufacturer | Chemical name | Function | wt. % |
|---|---|---|---|---|
| Deionized water | | water | solvents | 72.4 |
| Rewoquat WE 18 | Evonic Goldschmidt Ltd. | dialkyl ester ammonium ethosulfate | cationic surfactant | 16.6 |
| Mergal K9N | Honeywell Austria GmbH | 5-chloro-2-methyl-3-(2H)-isothiazolones and 2-methyl-3-(2H)-isothiazolone | preservative | 0.10 |
| Dow Corning 1520 Antifoam | Dow Corning GmbH. Germany | polydimethyl siloxane | defoamer | 0.30 |
| Magnesium chloride 1% solution | | magnesium chloride solution | consistency enhancer | 10.00 |
| Perfume oil C1 or C2 | Symrise | | perfume (fragrance) | 0.60 |

Perfume Oils for this Fabric Softener

| Fragrances | Perfume oil C1 comparative | Perfume oil C2 inventive |
|---|---|---|
| ALDEHYDE C10 | 0.5 | 0.5 |
| ALDEHYDE C11 ISO | 2.0 | 2.0 |
| ALDEHYDES C11 UNDECYLENIC | 12.0 | 12.0 |
| ALDEHYDE C12 MNA | 6.0 | 6.0 |
| FARENAL ® | 1.0 | 1.0 |
| VERTOCITRAL | 8.0 | 8.0 |
| ALLYL AMYL GLYCOLATE | 1.0 | 1.0 |
| STYRALYL ACETATE | 1.5 | 1.5 |
| DIHYDRO MYRCENOL | 65.0 | 65.0 |
| AGRUNITRIL | 1.0 | 1.0 |
| PEONILE | 15.0 | 15.0 |
| METHYL ANTHRANILATE | 10.0 | 10.0 |
| NEROLIONE 10% DPG | 1.5 | 1.5 |
| ROSEMARY OIL BM | 7.0 | 7.0 |
| SAGE OFFICINALE OIL DALM. | 3.0 | 3.0 |
| ISOBORNYL ACETATE | 40.0 | 40.0 |
| PRENYL ACETATE | 0.5 | 0.5 |
| ISOAMYL BUTYRATE | 0.5 | 0.5 |
| ALDEHYDE C14 SO-CALLED | 5.0 | 5.0 |
| MANZANATE | 0.5 | 0.5 |
| MUGETANOL | 5.0 | 5.0 |
| DIMETHYL BENZYL CARBINYL ACETATE | 2.5 | 2.5 |
| ROSE OXIDE D | 3.0 | 3.0 |
| ANTHER | 0.5 | 0.5 |
| PHENYLETHYL ALCOHOL | 35.0 | 35.0 |
| CITRONELLOL 950 | 15.0 | 15.0 |
| GERANIOL 60 | 10.0 | 10.0 |
| ISODAMASCON ® | 2.0 | 2.0 |
| ROSACETATE | 35.0 | 35.0 |
| CRESYL METHYL ETHER PARA | 0.5 | 0.5 |
| BENZYL ACETATE | 20.0 | 20.0 |
| HEXYL CINNAMIC ALDEHYDE ALPHA | 40.0 | 40.0 |
| METHYL BENZOATE | 1.0 | 1.0 |
| AMYL SALICYLATE N/ISO | 10.0 | 10.0 |
| BENZYL SALICYLATE | 70.0 | 70.0 |
| MYSORE ACETATE | 15.0 | 15.0 |
| PARMANYL ® | 0.5 | 0.5 |
| EUGENOL | 10.0 | 10.0 |
| ETHYL VANILLIN | 0.5 | 0.5 |
| COUMARIN | 3.0 | 3.0 |
| AGRUMEX HC | 45.0 | 45.0 |
| ARBAFLORATE | 25.0 | 25.0 |
| AMBERWOOD ® F | 5.0 | 5.0 |
| ISO E SUPER | 170.0 | 170.0 |
| PATCHOULI OIL DECOL. | 2.5 | 2.5 |
| SANDRANOL ® | 10.0 | 10.0 |
| ISOBUTYL QUINOLINE | 1.0 | 1.0 |
| EVERNYL | 0.5 | 0.5 |
| AMBROXIDE | 1.0 | 1.0 |
| GALAXOLIDE 50% IN IPM | 120.0 | 120.0 |
| INDOFLOR ® CRYST. | 0.5 | 0.5 |
| MESACONIC ACID DIETHYL ESTER | — | 60.0 |
| DIPROPYLENE GLYCOL | 220.0 | 160.0 |
| | 1,000.0 | 1,000.0 |

The addition of mesaconic acid diethyl ester (MSDEE) to the fragrance composition results in a more natural, round, transparent and fruity note.

Example 4: Soap

| Material | Manufacturer | Chemical name | Function | wt. % |
|---|---|---|---|---|
| Deionized water | | water | solvents | 2.0 |
| Soap Bases Mix | various | sodium tallowates/palmitates | surfactants | 95.8 |
| Titanium Dioxide | Kronos Titan GmbH. Germany | titanium dioxide | Dyestuff/brightener | 1.0 |
| Perfume oil D1 or D2 | Symrise | | Perfume (Fragrance) | 1.2 |

Perfume Oils for this Soap

| Fragrances | Perfume oil D1 (comparative) | Perfume oil D2 (as invented) |
|---|---|---|
| ALDEHYDE C 8 | 10.0 | 10.0 |
| ALDEHYDE C10 | 14.0 | 14.0 |
| ALDEHYDE C11 UNDECYLIC | 5.0 | 5.0 |
| ALDEHYDE C12 MNA | 4.0 | 4.0 |
| ISOAMYL ALCOHOL | 6.0 | 6.0 |
| VERTOCITRAL | 4.0 | 4.0 |
| ALLYL AMYL GLYCOLATE | 4.0 | 4.0 |
| DIHYDRO MYRCENOL | 120.0 | 120.0 |
| CITRAL 95 | 30.0 | 30.0 |
| AGRUNITRIL | 80.0 | 80.0 |
| CITRONITRILE | 40.0 | 40.0 |
| CITRYLAL | 4.0 | 4.0 |
| ORANGE OIL TERPENES | 250.0 | 250.0 |
| METHYL ANTHRANILATE | 1.5 | 1.5 |
| TERPINEOL HEAD FRACTION | 10.0 | 10.0 |
| EUCALYPTOL NAT. | 10.0 | 10.0 |
| THYMOL CRYST | 6.0 | 6.0 |
| BORNYL ACETATE L CRYST. | 82.5 | 82.5 |
| CAMPHOR DL | 20.0 | 20.0 |
| JASMAPRUNATE | 5.0 | 5.0 |
| ALDEHYDE C14 SO-CALLED | 2.0 | 2.0 |
| MANZANATE | 0.5 | 0.5 |
| ALLYL HEPTOATE | 2.5 | 2.5 |
| ROSE OXIDE L | 0.5 | 0.5 |
| DAMASCONE ALPHA | 0.5 | 0.5 |
| HEDIONE | 10.0 | 10.0 |
| AMYL SALICYLATE N/ISO | 60.0 | 60.0 |
| HEXYL SALICYLATE | 35.0 | 35.0 |
| COUMARIN | 2.5 | 2.5 |
| AGRUMEX HC | 30.0 | 30.0 |
| ORYCLON SPECIAL | 55.0 | 55.0 |
| PATCHOULI OIL DECOL. | 2.0 | 2.0 |
| SANDRANOL ® | 1.5 | 1.5 |
| TONALIDE | 2.0 | 2.0 |
| MESACONIC ACID DIETHYL ESTER | — | 40.0 |
| DIPROPYLENE GLYCOL | 130.0 | 90.0 |
|  | 1,000.0 | 1,000.0 |

The addition of mesaconic acid diethyl ester (MSDEE) results in more natural, transparent, pear-like and fruity notes. Furthermore, mesaconic acid diethyl ester gives the composition more strength and fullness.

Example 5: Pearl-Lustre Shampoo

| Material | Manufacturer | INCI name | wt. % |
|---|---|---|---|
| Deionized water |  | water | 71.5 |
| Plantacare PS 10 | BASF Personal Care & Nutrition GmbH | sodium laureth sulfates, Lauryl Glucosides | 20.0 |
| Euperlan PK 771 | BASF Personal Care & Nutrition GmbH | glycol distearates, sodium lauryl sulfates, cocamides MEA, Laureth-10 | 6.0 |
| Dragocid Liquid | Symrise AG | phenoxyethanol, methylparaben, ethylparaben, butylparaben, propylparaben, isobutylparaben | 0.5 |
| sodium chloride |  | sodium chloride | 1.4 |
| Citric acid monohydrate crystalline |  | citric acid | 0.1 |
| Perfume oil G1 or G2 | Symrise AG | Perfume (Fragrance) | 0.5 |

Perfume Oils for this Pearlescent Shampoo:

| Fragrances | Perfume oil G1 (comparative) | Perfume oil G2 (as invented) |
|---|---|---|
| FARENAL ® | 3.0 | 3.0 |
| FLORAZON | 0.5 | 0.5 |
| HEXENYL ACETATE CIS-3 | 3.0 | 3.0 |
| VERTOCITRAL | 1.0 | 1.0 |
| DYNASCONE 10% DPG | 2.0 | 2.0 |
| CYCLOGALBANAT ® | 2.0 | 2.0 |
| STYRALYL ACETATE | 1.5 | 1.5 |
| DIHYDRO MYRCENOL | 6.0 | 6.0 |
| OXANTHIA 50% IN TEC 10% DPG | 10.0 | 10.0 |
| LEMON OIL ITAL. | 10.0 | 10.0 |
| ORANGE OIL BRASIL | 50.0 | 50.0 |
| HEXYL ACETATE | 2.0 | 2.0 |
| ISOAMYL ACETATE | 0.5 | 0.5 |
| PRENYL ACETATE | 0.5 | 0.5 |
| ETHYL BUTYRATE 10% DPG | 2.0 | 2.0 |
| ALDEHYDE C14 SO-CALLED | 25.0 | 25.0 |
| DECALACTONE GAMMA | 5.0 | 5.0 |
| ETHYL METHYL BUTYRATE-2 | 1.0 | 1.0 |
| ALLYL CAPROATE | 1.5 | 1.5 |
| ALLYL CYCLOHEXYL PROPIONATE | 3.0 | 3.0 |
| ALLYL HEPTOATE | 2.5 | 2.5 |
| MELOZONE | 2.0 | 2.0 |
| CALONE 1951 | 0.5 | 0.5 |
| MUGETANOL | 10.0 | 10.0 |
| LINALOOL | 25.0 | 25.0 |
| DIMETHYL BENZYL CARBINYL ACETATE | 6.0 | 6.0 |
| DIMETHYL BENZYL CARBINYL BUTYRATE | 4.0 | 4.0 |
| PHENYLETHYL ACETATE | 1.5 | 1.5 |
| PHENYLETHYL ALCOHOL | 15.0 | 15.0 |
| CITRONELLOL 950 | 10.0 | 10.0 |
| GERANIOL SUPER | 5.0 | 5.0 |
| GERANYL ACETATE PURE | 15.0 | 15.0 |
| ISODAMASCON ® | 2.0 | 2.0 |
| BENZYL ACETATE | 15.0 | 15.0 |
| HEDIONE | 90.0 | 90.0 |
| HEXYL CINNAMIC ALDEHYDE ALPHA | 35.0 | 35.0 |
| JASMONE CIS | 0.5 | 0.5 |
| BENZYL SALICYLATE | 80.0 | 80.0 |
| HEXENYL SALICYLATE CIS-3 | 30.0 | 30.0 |
| ISORALDEINE 70 | 35.0 | 35.0 |
| ARBAFLORATE | 15.0 | 15.0 |
| ISO E SUPER | 15.0 | 15.0 |
| ISOBORNYL CYCLOHEXANOL | 30.0 | 30.0 |
| BRAHMANOL ® | 10.0 | 10.0 |
| AMBROXIDE | 1.5 | 1.5 |
| GLOBALIDE | 5.0 | 5.0 |
| GALAXOLIDE 50% IN DPG | 120.0 | 120.0 |
| MESACONIC ACID DIETHYL ESTER | — | 65.0 |
| DIPROPYLENE GLYCOL | 290.0 | 225.0 |
|  | 1,000.0 | 1,000.0 |

With a dosage of 0.5% of the perfume oil in the shampoo, the following results are obtained: the addition of mesaconic acid diethyl ester (MSDEE) to perfume oil G2 strengthens the radiant fruity character. In addition, the diffusivity is increased.

Example 6: Transparent Deodorant Sticks (Formulation A, B) or Deodorant Cream Sticks (Formulation C, D)

| Component (in wt. %) | A | B | C | D |
|---|---|---|---|---|
| aluminium zirconium tetrachlorohydrate-glycine complex | 25.00 | 20.00 | 25.00 | 20.00 |
| dimethicone (10 Cst) | — | — | 5.00 | 5.00 |
| cyclopentasiloxane | — | 0.50 | 1.00 | 0.50 |
| petroleum jelly | 5.00 | 4.70 | 5.00 | 5.00 |
| ozokerite | 1.00 | 1.50 | — | — |
| stearyl alcohol | 12.00 | 12.00 | — | — |
| 2-butyloctanoic acid | 0.50 | — | 0.50 | — |
| wax | — | — | 1.25 | 1.25 |
| PPG-14 butyl ether | 9.00 | 9.00 | — | — |
| Hardened rapeseed oil | — | — | 5.00 | 5.00 |
| silicon dioxide | — | — | 1.00 | — |
| farnesol | 0.25 | — | 0.25 | — |
| paraffin oil | 0.50 | 0.50 | — | — |
| hydrogenated castor wax oil | 3.50 | 3.50 | — | — |
| talc | 4.00 | 4.00 | — | — |
| behenyl alcohol | 0.20 | 0.20 | — | — |
| d-panthenyl triacetate | 1.00 | 1.00 | — | — |
| preserving agent | q.s. | q.s. | q.s. | q.s. |
| perfume oil H1 or H2 | 1.50 | — | 1.15 | — |
| perfume oil G2 from example 5 | — | 0.90 | — | 0.75 |
| water | Ad 100 | Ad 100 | Ad 100 | Ad 100 |

Perfume Oils for Transparent Deodorant Sticks or Deodorant Cream Sticks

| Fragrances | Perfume oil H1 (comparative) | Perfume oil H2 (as invented) |
|---|---|---|
| ALDEHYDE C10 | 0.5 | 0.5 |
| ALDEHYDE C12 MNA 10% DPG | 2.0 | 2.0 |
| MINTONAT | 40.0 | 40.0 |
| MELOZONE | 0.5 | 0.5 |
| VERTOCITRAL | 6.0 | 6.0 |
| DIHYDRO MYRCENOL | 120.0 | 120.0 |
| TETRAHYDRO MYRCENOL | 10.0 | 10.0 |
| AGRUNITRIL | 1.0 | 1.0 |
| ORANGE OIL BRASIL | 10.0 | 10.0 |
| TAMARINE TYPE BASE | 10.0 | 10.0 |
| HEXYL ACETATE | 6.0 | 6.0 |
| ALDEHYDE C14 SO-CALLED | 1.0 | 1.0 |
| TETRAHYDRO LINALOOL | 40.0 | 40.0 |
| DIMETHYL BENZYL CARBINYL BUTYRATE | 5.0 | 5.0 |
| ORANGE FLOWER ETHER | 5.0 | 5.0 |
| PHENYLETHYL ACETATE | 6.5 | 6.5 |
| PHENYLETHYL ALCOHOL | 15.0 | 15.0 |
| GERANIOL SUPER | 30.0 | 30.0 |
| ROSAPHEN ® | 25.0 | 25.0 |
| ISODAMASCON ® | 0.5 | 0.5 |
| HEDIONE | 300.0 | 300.0 |
| UNDECAVERTOL | 0.5 | 0.5 |
| ALLYL IONONE | 2.5 | 2.5 |
| IONONE BETA | 10.0 | 10.0 |
| EUGENOL | 4.0 | 4.0 |
| ISO E SUPER | 30.0 | 30.0 |
| BRAHMANOL ® | 2.0 | 2.0 |
| AMBROXIDE | 2.0 | 2.0 |
| GLOBALIDE | 12.0 | 12.0 |
| GLOBANONE | 8.0 | 8.0 |
| MACROLIDE ® SUPRA | 45.0 | 45.0 |
| MESACONIC ACID DIETHYL ESTER | — | 50.0 |
| DIPROPYLENE GLYCOL | 300.0 | 250.0 |
|  | 1,000.0 | 1,000.0 |

Example 7: Hair Conditioner with UV Protection

| Component | INCI Name | wt. % | wt. % |
|---|---|---|---|
| Lanette O | cetearyl alcohol | 4.00 | 4.00 |
| Dragoxat 89 | ethylhexyl isononanoates | 4.00 | 4.00 |
| Emulsiphos | potassium cetyl phosphates, hydrogenated palm glycerides | 0.50 | 0.50 |
| Natrosol 250 HR | hydroxyethyl cellulose | 0.25 | 0.25 |
| Neo Heliopan Hydro | phenylbenzimidazole sulfonic acid | 2.00 | 2.00 |
| L-arginine | arginine | 1.20 | 1.20 |
| benzophenone-4 | benzophenone-4 | 0.50 | 0.50 |
| Neo Heliopan AP | disodium phenyl dibenzimidazole tetrasulfonate | 0.50 | 1.00 |
| Edeta BD | disodium EDTA | 0.05 | 0.05 |
| Dragocide Liquid | phenoxyethanol (and) methylparaben (and) butyparaben (and) ethyparaben (and) propylparaben | 0.80 | 0.80 |
| Dow Corning 949 Cationic Emulsion | amodimethicone, cetrimonium chloride, trideceth-12 | 2.00 | 2.00 |
| Dow Corning 5200 | laurylmethicone copolyol | 0.50 | 0.50 |
| Perfume oil B2 from example 2 | perfume | 0.95 | — |
| Perfume oil H2 from example 6 | perfume | — | 1.25 |
| water | water (Aqua) | Ad 100 | Ad 100 |

Example 8: Sunscreen Milk (W/O)

| part | raw materials | INCI designation | wt. % |
|---|---|---|---|
| A | Dehymuls PGPH | Polyglyceryl-2 dipolyhydroxystearate | 3.00 |
|  | Beeswax 8100 | Beeswax | 1.00 |
|  | Monomuls 90-O-18 | Glyceryl Oleate | 1.00 |
|  | Zinc stearate | Zinc stearate | 1.00 |
|  | Cetiol SN | Cetearyl Isononanoate | 5.00 |
|  | Cetiol OE | Dicaprylyl Ether | 5.00 |
|  | Tegosoft TN | C12-15 alkyl benzoate | 4.00 |
|  | Vitamin E | Tocopherol | 0.50 |
|  | Solbrol P | Propyl Paraben | 0.10 |
|  | Neo Heliopan ® OS | Ethylhexyl Salicylate | 5.00 |
|  | Neo Heliopan ® AV | Ethylhexyl Methoxycinnamate | 7.50 |
|  | Uvinul ® T150 | Ethylhexyl Triazone | 1.50 |
| B | Water, distilled | Water (Aqua) | Ad 100 |
|  | Trilon BD | Disodium EDTA | 0.10 |
|  | Glycerin | Glycerin | 5.00 |
|  | Solbrol M | Methylparaben | 0.20 |
|  | Phenoxyethanol | Phenoxyethanol | 0.70 |
|  | Neo Heliopan ® AP 10% solution, neutralized with NaOH | Disodium Phenyl Dibenzimidazole Tetrasulfonate | 15.00 |
| C | Perfume oil C2 from example 3 | Perfume (Fragrance) | 0.25 |
|  | Alpha Bisabolol | Bisabolol | 0.10 |

Manufacturing Techniques

Part A: Heat to approx. 85° C.

Part B: Heat to approx. 85° C. Add B to A. Allow to cool while stirring.

Part C: Add and then homogenise.

Example 9: Hair Coloring Cream for a Blonde Shade

| PArt | Material | Manufacturer | INCI name | wt. % |
|---|---|---|---|---|
| A | Oxowax | LCW, France | Cethyl alcohol, Oleyl alcohol, Cetearyl alcohol, Stearic acid | 21.00 |
|  | Volpo CS 25 | Croda GmbH, Germany | Ceteareth25 | 4.00 |
|  | Berol 175 | Brenntag Eurochem GmbH, Germany | Laureth-8 | 10.00 |
|  | Lanette ® E | BAST Personal Care & Nutrition GmbH | Sodium Cetearyl Sulfate | 1.00 |
|  | Covaquat 16 | LCW, France | Polyquaternium-6 | 4.00 |
|  | Water |  | Water (Aqua) | 49.30 |
| B | Ammonia (20% in water) | Merk Eurolab | Ammonia | 10.20 |
| C | Perfume oil D2 from example 4 | Symrise AG | Perfume | 0.50 |

Mix parts A, B and C other than Covaquat 16 together and heat at 80° C. for 20 minutes. After the product is homogeneous let it cool down. Add Covaquat 16 at 50° C. When the product starts to thicken stop stirring. Add NH$_4$OH at room temperature and stir until homogenized.

Example 10: Candle

| Material | wt. % |
|---|---|
| Candle wax | 95.00 |
| Perfume oil D2 from example 4 | 5.00 |

Melt the candle wax and stir. Add the perfume oil and stir well. Pour into the desired mould.

Example 11: Perfume Oils for Eau De Toilette (10% in Ethanol)

|  | J1 (comparative example) | J2 (example according to invention) |
|---|---|---|
| ACETOACETIC ACID ETHYL ESTER | 50 | 50 |
| FLORALOZONE 10% DPG | 50 | 50 |
| HEXENOL CIS-3 | 30 | 30 |
| HEXENYLACETATE CIS-3 10% DPG | 10 | 10 |
| LEAFOVERT ® | 20 | 20 |
| CYCLOGALBANAT ® 10% DPG | 30 | 30 |
| MAGNOLAN | 305 | 305 |
| STYROLYLACETATE | 20 | 20 |
| METHYLANTHRANILATE 10% DPG | 20 | 20 |
| RED BERRIES EXTRACT | 30 | 30 |
| ALDEHYDE C14 SO-CALLED EXTRA | 20 | 20 |
| ETHYLMETHYLBUTYRATE-2 1% DPG | 30 | 30 |
| MANZANATE 1% DPG | 50 | 50 |
| APRIFLOREN ® | 10 | 10 |
| DAVANAOEL F. PARF. 10% DPG | 30 | 30 |
| CASSIS 345F TYPE BASE | 20 | 20 |
| LILIAL | 100 | 100 |
| CALONE 1% DPG | 100 | 100 |
| HELIONAL | 200 | 200 |
| FLOROSA | 300 | 300 |
| ETHYLLINALOOL | 470 | 470 |
| ROSE OXIDE D 10% DPG | 50 | 50 |
| PHENYLETHYL ALCOHOL PURE | 20 | 20 |
| CITRONELLOL 950 | 50 | 50 |
| DAMASCENONE 10% DPG | 30 | 30 |
| ROSACETATE | 10 | 10 |
| HEDIONE HC/70 | 1,500.00 | 1,400.00 |
| UNDECAVERTOL | 30 | 30 |
| IONON BETA | 230 | 230 |
| ISO E SUPER NON DISCOLORING | 300 | 300 |
| EVERNYL 10% DPG | 10 | 10 |
| AMBROXIDE | 50 | 50 |
| ETHYLENE BRASSYLATE | 1,000.00 | 1,000.00 |
| GLOBALIDE | 600 | 500 |
| GLOBANONE | 400 | 400 |
| GALAXOLID PURE | 1,800.00 | 1,800.00 |
| TONALID | 500 | 500 |
| MESACONIC ACID DIETHYL ESTER |  | 200 |
| INDOLE FF 10% DPG | 25 | 25 |

The chord with mesaconic acid diethyl ester gives a natural intense pear-like impression.

Example 12: Perfume Oils for Eau De Toilette (10% in Ethanol)

|  | K1 (comparative example) | K2 (example according to invention) |
|---|---|---|
| ACETOACETIC ACID ETHYL ESTER | 10 | 10 |
| HEXENOL CIS-3 | 2.5 | 2.5 |
| HEXENYLACETATE CIS-3 1% DPG | 4 | 4 |
| LEAFOVERT ® 10% DPG | 5 | 5 |
| VERTOCITRAL 10% DPG | 4 | 4 |
| PHENYLACETALDEHYDE DIMETHYLACETAL 10% DPG | 3 | 3 |
| CYCLOGALBANAT ® 10% DPG | 6 | 6 |
| MAGNOLAN | 9 | 9 |
| STYROLYLACETATE | 1 | 1 |
| DIHYDROMYRCENOL | 6 | 6 |
| LINALYLACETATE | 36 | 36 |
| ITAL. CITRIC OIL | 10 | 10 |
| ORANGE OIL ITAL.SWEET UNF. | 2 | 2 |
| AMAROCIT ® | 1 | 1 |
| OXANE 1% DPG | 3 | 3 |
| METHYLANTHRANILATE 10% DPG | 1 | 1 |
| ISOAMYLACETATE | 1 | 1 |
| ALDEHYDE C14 SOG | 1.5 | 1.5 |
| DECALACTONE GAMMA 10% DPG | 2 | 2 |
| CASSIS BASE 345 BB | 10 | 10 |
| FRAMBINON | 1.5 | 1.5 |
| ETHYLMALTOL | 50 | 50 |
| BOURGEONAL | 2.5 | 2.5 |
| HELIONAL | 5 | 5 |
| FLOROSA BM/PYRANOL | 55 | 50 |
| HYDROXYCITRONELLAL | 20 | 20 |
| ETHYLLINALOOL | 38 | 33 |
| LINALOOL | 14 | 14 |
| DIMETHYLBENZYLCARB-INYLBUTYRATE | 5 | 5 |
| ROSE OXIDE | 1.5 | 1.5 |
| PHENIRAT ® | 3 | 3 |
| PHENYLETHYL ALCOHOL | 1 | 1 |
| PHENYLETHYLISOBUTYRATE 10% DPG | 3 | 3 |
| CITRONELLOL 950 | 2 | 2 |

| | K1 (comparative example) | K2 (example according to invention) |
|---|---|---|
| GERANIOL SUPRA | 3 | 3 |
| NEROL 900 | 2 | 2 |
| CITRONELLYL FORMATE 10% DPG | 5 | 5 |
| GERANYL FORMATE SUPRA | 1 | 1 |
| DAMASCENONE | 1 | 1 |
| DAMASCON ALPHA 10% DPG | 3 | 3 |
| BENZYLACETATE | 6.5 | 6.5 |
| HEDIONE HC/30 | 69 | 69 |
| HEXYLCINNAMIC ALDEHYDE ALPHA | 2 | 2 |
| JASMINLACTONE | 1.5 | 1.5 |
| BENZYLSALICYLATE | 32 | 32 |
| HEXENYLSALICYLATE CIS-3 | 13 | 13 |
| DIHYDROIONONE BETA | 15 | 15 |
| ISORALDEIN 95 | 8 | 8 |
| ETHYLVANILLIN | 36 | 36 |
| VANILLIN | 19 | 19 |
| CINNAMYL ALCOHOL | 1 | 1 |
| COUMARIN | 4 | 4 |
| AGRUMEX LC | 1 | 1 |
| CASHMERAN | 12 | 12 |
| CEDRAMBER | 12 | 12 |
| ISO E SUPER | 150 | 150 |
| TRIMOFIX O | 15 | 15 |
| PATCHOULI OIL ENTF. DM | 22 | 22 |
| ISOBORNYLCYCLOHEXANOL | 35 | 35 |
| AMBROXIDE | 3 | 3 |
| AMBRETTOLIDE | 8 | 8 |
| MACROLIDE ® SUPRA | 22 | 22 |
| GALAXOID 50% IN IPM | 52.5 | 52.5 |
| HELVETOLIDE | 20 | 20 |
| INDOLE FF 10% DPG | 3 | 3 |
| MESACONIC ACID DIETHYL ESTER | | 10 |
| BENZYL ALCOHOL DD | 3 | 3 |

The base note is clearly more pear-like with mesaconic acid diethyl ester.

Example 13: Perfume Oil for Eau De Toilette (10% in Ethanol)

| | L1 (comparative example) | L2 (example according to invention) |
|---|---|---|
| ACETOACETIC ACID ETHYL ESTER | 1 | 1 |
| HEXENOL CIS-3 10% DPG | 5 | 5 |
| HEXENYLACETATE CIS-3 10% DPG | 4 | 4 |
| HEXENYLISOBUTYRATE CIS-3 10% DPG | 5 | 5 |
| LEAFOVERT ® 10% DPG | 5 | 5 |
| STYROLYLACETATE | 2 | 2 |
| BERGAMOT OIL REAL | 5 | 5 |
| LINALYLACETATE | 20 | 20 |
| ORANGE OIL GUINEA | 2 | 2 |
| AMAROCIT ® | 6 | 6 |
| BUTYL ACETATE 10% DPG | 1 | 1 |
| HEXYLACETATE | 4 | 4 |
| ISOAMYL ACETATE 10% DPG | 1 | 1 |
| PRENYL ACETATE 10% DPG | 2 | 2 |
| ALDEHYDE C14 SO-CALLED EXTRA | 2 | 2 |
| DECALACTONE GAMMA | 1.5 | 1.5 |
| MANZANATE 1% DPG | 5 | 5 |
| WINE YEAST OIL GREEN MAXIMAROME 1% DPG | 5 | 5 |
| ETHYLMALTOL | 10 | 10 |
| MALTOL | 2.5 | 2.5 |
| BOURGEONAL | 1 | 1 |
| CYCLAMENALDEHYDE | 1.5 | 1.5 |
| HELIONAL | 5 | 5 |
| FLOROSA | 40 | 40 |
| HYDROXYCITRONELLAL | 5 | 5 |
| ETHYLLINALOOL | 20 | 20 |
| LINALOOL | 15 | 15 |
| DIMETHYLBENZYLCARBINYL ACETATE | 2 | 2 |
| PHENYLETHYL ALCOHOL PURE | 5 | 5 |
| CITRONELLOL 950 | 8 | 8 |
| GERANIOL SUPRA | 5 | 5 |
| CITRONELLA ACETATE EXTRA | 5 | 5 |
| GERANYLACETATE PURE | 10 | 10 |
| NERYLACETATE | 5 | 5 |
| DAMASCENONE TOTAL 10% DPG | 5 | 5 |
| DAMASCON ALPHA 10% DPG | 6 | 6 |
| BENZYLACETATE FG | 2 | 2 |
| HEDIONE | 120 | 100 |
| HEXYLCINNAMIC ALDEHYDE ALPHA | 6 | 6 |
| JASMON CIS 10% DPG | 3 | 3 |
| BENZYLSALICYLATE | 30 | 30 |
| HEXENYLSALICYLATE CIS-3 | 10 | 10 |
| HEXYLSALICYLATE | 30 | 30 |
| UNDECAVERTOL | 2 | 2 |
| ISORALDEIN 95 | 10 | 10 |
| ISOEUGENOL ACETATE 10% DPG | 3 | 3 |
| ETHYLVANILLIN 10% DPG | 1 | 1 |
| VANILLIN | 3 | 3 |
| CINNAMON TALKOHOL | 2 | 2 |
| CUMARIN | 3 | 3 |
| AGRUMEX HC | 5 | 5 |
| CEDAR WOOD OIL VIRGINIA | 10 | 10 |
| AMBERWOOD ® F | 10 | 10 |
| CASHMERAN | 10 | 10 |
| ISO E SUPER NON DISCOLORING | 85 | 85 |
| POLYSANTOL (MYSANTOL) | 5 | 5 |
| AMBROXIDE | 8 | 8 |
| AMBRETTOLIDE | 10 | 10 |
| GLOBALIDE | 10 | 10 |
| MACROLIDE ® SUPRA | 50 | 50 |
| GALAXOID 50% IN IPM | 115 | 105 |
| HELVETOLIDE | 10 | 10 |
| MESACONIC ACID DIETHYL ESTER | | 30 |
| DIPROPYLENE GLYCOL | 19.5 | 19.5 |

Stronger fruity pear smell with mesaconic acid diethyl ester.

Example 14: Sensory and Physicochemical Evaluation of Mesaconic Acid Diethyl Ester

| Test | Scale | Mesaconic acid diethyl ester |
|---|---|---|
| Threshold value in DEP [1] | 1-13 | 6.3 |
| Effect on blotting paper [1] | 1-9 | 5 |
| Dwell time on blotting paper [1] | 1-9 | 2.7 |
| Threshold value in air [1] | 5-13 | 6.4 |
| Threshold value in air [1] | ppm | 0.047 |
| Intensity in air [1] | 1-9 | 4 |
| Diffuseness | 1-9 | 7.2 |
| Flowering from water [1] | 1-9 | 6 |
| Anosmia [2] | % | 0 |
| Water solubility [3] | 1-9 | 6.2 |

-continued

| Test | Scale | Mesaconic acid diethyl ester |
|---|---|---|
| Polarity [4] | 1-9 | 3.4 |
| Volatility [5] | 1-9 | 6.4 |
| Estimated stability alkalis [6] | | |
| Estimated stability acids [6] | | |
| Estimated stability against oxidation [6] | | |
| Reduction of bathroom odour [8] | 0-7 | 4.1 |
| Scent intensity in the bathroom [9] | 1-9 | 5.4 |
| Reduction of kitchen odour [8] | 0-7 | 4.5 |
| Scent intensity in the kitchen [9] | 1-9 | 4.9 |
| Reduction of sweat odour [8] | 0-7 | 4.2 |
| Scent intensity sweat [9] | 1-9 | 5.1 |
| Reduction of smoke odour [8] | 1-7 | 3.5 |
| Fragrance intensity smoke [9] | 1-9 | 4.5 |

In this context:
[1] The higher the value, the higher the olfactory performance.
[2] Percentage of subjects unable to perceive the odour
[3] The higher the value, the higher the water solubility.
[4] The higher the value, the lower the polarity.
[5] The higher the value, the higher the volatility, the lower the value, the higher the adhesion.
[6] Classification: high-moderate-low
[7] Standard: Linalool (value = 5)
[8] Scale 1 (strong unpleasant odor) to 7 (no unpleasant odor)
[9] Scale 1 (no odor) to 9 (strong odor)

Example 15: Stability Studies

Mesaconic acid diethyl ester (MSDEE) was stored alone and as a component of various formulations for 24 and 72 hours respectively under drastic conditions at 60° C. and 5 bar pressure. The remaining amount of active substance was then determined. The results are summarised in Table 3 below:

TABLE 3

Storage stability

| Product | Proportion MSDEEE [wt. %] | After 24 h [%] | After 72 h [%] |
|---|---|---|---|
| MSDEE | 100 | 98 | 98 |
| eau de toilette | 4.5 | 99 | 99 |
| deodorant | 0.5 | 94 | 48 |
| shampoo | 0.5 | 100 | 100 |
| fabric softener | 0.5 | 92 | 89 |

The invention claimed is:

1. A fragrance mixture comprising a sensory effective amount of two or all three compounds selected from the group consisting of: formula (i), formula (ii) and formula (iii):

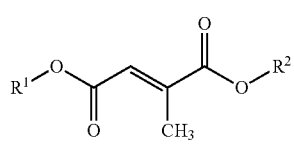

formula (i)

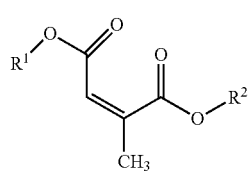

formula (ii)

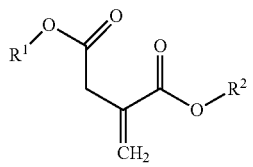

formula (iii)

wherein $R^1$ each represents a linear, branched or cyclic alkyl radical having 1 to 10 carbon atoms, an araliphatic or aromatic radical, and
wherein $R^2$ each represents a linear, branched or cyclic alkyl radical having 1 to 10 carbon atoms, an araliphatic or aromatic radical.

2. The fragrance mixture according to claim 1, wherein $R^1$ and $R^2$ in the compounds of formula (i), formula (ii) and formula (iii) are each the same radical.

3. The fragrance mixture according to claim 1, wherein $R^1$ and $R^2$ are each independently selected from the group consisting of: linear or branched methyl, ethyl, propyl, and butyl alkyl radicals.

4. The fragrance mixture according to claim 1, wherein the compounds of formula (i), formula (ii) and formula (iii) are each as follows:
   (i) (E)-2-methyl-but-2-endicarboxylic acid diethyl ester,
   (ii) (2)-2-methyl-but-2-endicarboxylic acid diethyl ester, and
   (iii) 2-Methylenebutanedicarboxylic acid diethyl ester.

5. The fragrance mixture according to claim 1, characterized in that it contains the compound of formula (i), relative to the sum of the compounds of formula (i), formula (ii) and formula (iii), in an amount of 50 to 100% by weight.

6. The fragrance mixture according to claim 1, characterized in that it contains two or all three compounds selected from the group consisting of formula (i), formula (ii) and formula (iii) that together amount to 0.001 to 99.999 wt. % based on the fragrance mixture.

7. The fragrance mixture according to claim 1, characterized in that it contains one or more further fragrances selected from the group consisting of:
   (1) Hydrocarbons;
   (2) Aliphatic alcohols;
   (3) Aliphatic aldehydes and their acetals;
   (4) Aliphatic ketones and their oximes;
   (5) Aliphatic sulphur-containing compounds;
   (6) Aliphatic nitriles;
   (7) Esters of aliphatic carboxylic acids;
   (8) Acyclic terpene alcohols;
   (9) Acyclic terpene aldehydes and ketones;
   (10) Cyclic terpene alcohols;
   (11) Cyclic terpene aldehydes and ketones;
   (12) Cyclic alcohols;
   (13) Cycloaliphatic alcohols;
   (14) Cyclic and cycloaliphatic ethers;
   (15) Cyclic and macrocyclic ketones;
   (16) Cycloaliphatic aldehydes;
   (17) Cycloaliphatic ketones;
   (18) Esters of cyclic alcohols;
   (19) Esters of cycloaliphatic alcohols;
   (20) Esters of cycloaliphatic carboxylic acids;
   (21) Araliphatic alcohols;
   (22) Esters of araliphatic alcohols and aliphatic carboxylic acids;
   (23) Araliphatic ethers;
   (24) Aromatic and araliphatic aldehydes;

(25) Aromatic and araliphatic ketones;
(26) Aromatic and araliphatic carboxylic acids and their esters;
(27) Nitrogen-containing aromatic compounds;
(28) Phenols, phenyl ethers and phenyl esters;
(29) Heterocyclic compounds;
(30) Lactones;
and their mixtures.

8. A perfume oil agent, cosmetic agent, application agent or washing and cleaning agent containing a fragrance mixture according to claim 1.

9. The agent according to claim 8, characterized in that it contains the fragrance mixture according to claim 1 in an amount of 0.05 to 5 wt. %, based on the agent.

10. The agent according to claim 8, characterized in that it is selected from the group consisting of: solid and liquid soaps, shower gels, shampoos, shaving soaps, shaving foams, bath oils, cosmetic emulsions, skin creams and lotions, face creams and lotions, sun protection creams and lotions, after-sun creams and lotions, hand creams and hand lotions, foot creams and lotions, depilatory creams and lotions, after-shave creams and lotions, tanning creams and lotions, hair sprays, hair gels, hair lotions, hair conditioners, permanent and semi-permanent hair dyes, hair deforming agents, hair tonics, hair creams and lotions, deodorants, underarm sprays, roll-ons, deodorant sticks, deodorant cremes and decorative cosmetic products as well as perfume extracts, eau de parfums, eau de toilettes, shaving lotions, eau de colognes, preshave products, splash-colognes, refreshing wipes, acidic, alkaline and neutral cleaning agents, floor cleaners, window glass cleaners, dishwashing detergents, bathroom and sanitary cleaners, scouring milk, solid and liquid WC cleaners, powdered and foamed carpet cleaners, liquid washing agents, powdered washing agents, laundry pretreatment agents, bleaching agents, soaking agents and stain removers, fabric softeners, washing soaps, washing tablets, disinfectants, surface disinfectants, air fresheners in liquid form, gel-like form or in a form applied on a solid carrier, aerosol sprays, furniture polishes, floor waxes, shoe polishes.

11. A method for imparting, modifying or enhancing a fruity, pear-like scent note in a fragrance mixture, a perfume oil, cosmetic agent, application agent or washing and cleaning agent, comprising the following steps:
(a1) providing two or more compounds of formula (i), formula (ii) and/or formula (iii) according to claim 1; and
(a2) mixing a sensory effective amount of the two or more compounds of (a1) with a mixture of additional fragrances sufficient to afford a fruity, pear-like scent in the finished preparation,
or
(b1) providing two or more compounds of formula (i), formula (ii) and/or formula (iii) according to any claim 1; and
(b2) mixing a sensory effective amount of the two or more compounds of (b1) with the perfume oil, cosmetic agent, application agent or washing and cleaning agent sufficient to afford a fruity, pear-like scent in the finished preparation.

12. A method of imparting, modifying or enhancing a fruity, pear-like scent in a fragrance mixture, a perfume oil, cosmetic agent, application agent or washing and cleaning agent, comprising adding two or more compounds in the group of formula (i), formula (ii) and formula (iii) according to claim 1 to a fragrance mixture, a perfume oil, cosmetic agent, application agent or washing and cleaning agent.

13. The method of claim 12, wherein the compounds of formula (i), formula (ii) and formula (iii) are each as follows:
(i) (E)-2-methyl-but-2-endicarboxylic acid diethyl ester,
(ii) (2)-2-methyl-but-2-endicarboxylic acid diethyl ester, and
(iii) 2-Methylenebutanedicarboxylic acid diethyl ester.

14. The fragrance mixture according to claim 6, characterized in that it contains two or all three compounds selected from the group consisting of formula (i), formula (ii) and formula (iii) that together amount to 0.05 to 50 wt. % based on the fragrance mixture.

* * * * *

UNITED STATES PATENT AND TRADEMARK OFFICE
CERTIFICATE OF CORRECTION

PATENT NO.        : 10,988,434 B2
APPLICATION NO.   : 16/471422
DATED             : April 27, 2021
INVENTOR(S)       : Vijayanand Chandrasekaran et al.

It is certified that error appears in the above-identified patent and that said Letters Patent is hereby corrected as shown below:

In the Claims

At Column 62, Line 28, "(2)" should be -- (Z) --.

At Column 64, Line 32, "(2)" should be -- (Z) --.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*